United States Patent
Van Rensburg et al.

(10) Patent No.: US 12,343,235 B2
(45) Date of Patent: Jul. 1, 2025

(54) TISSUE BORNE STACKABLE FOUNDATION GUIDE AND METHOD OF MAKING AND USING SAME

(71) Applicant: DDS Company, Inc., Durham, NC (US)

(72) Inventors: Cornelis J. Janse Van Rensburg, Durham, NC (US); Brian Lee, Durham, NC (US); Matthew Vrhovac, Durham, NC (US)

(73) Assignee: DDS Company, Inc., Durham, NC (US)

( * ) Notice: Subject to any disclaimer, the term of this patent is extended or adjusted under 35 U.S.C. 154(b) by 314 days.

(21) Appl. No.: 16/869,698

(22) Filed: May 8, 2020

(65) Prior Publication Data

US 2020/0352736 A1 Nov. 12, 2020

Related U.S. Application Data

(60) Provisional application No. 62/912,821, filed on Oct. 9, 2019, provisional application No. 62/872,829, filed (Continued)

(51) Int. Cl.
*A61C 8/00* (2006.01)
*A61B 17/17* (2006.01)
(Continued)

(52) U.S. Cl.
CPC .......... *A61C 8/0089* (2013.01); *A61B 17/176* (2013.01); *A61C 1/082* (2013.01);
(Continued)

(58) Field of Classification Search
CPC ......... A61C 1/082; A61C 1/084; A61C 1/085; A61C 8/0089; A61C 8/009; A61C 8/0092; A61C 13/0001; A61C 13/01; A61C 13/10
See application file for complete search history.

(56) References Cited

U.S. PATENT DOCUMENTS 1,417,237 A  5/1922  George
3,579,829 A * 5/1971 Sampson .............. A61C 8/0031
                                               433/173

(Continued)

FOREIGN PATENT DOCUMENTS

CN   105852931 A   8/2016
EP    1502556 A2   2/2005

(Continued)

OTHER PUBLICATIONS

Oh, KR101457011B1_Description_20241119_1351, 2014 (Year: 2014).*

(Continued)

*Primary Examiner* — Cris L. Rodriguez
*Assistant Examiner* — Sydney J Pulvidente
(74) *Attorney, Agent, or Firm* — Ward and Smith, P.A.; Ryan K. Simmons

(57) ABSTRACT

A tissue borne stackable foundation guide is provided. The foundation guide may include a main body; first connectors formed on and spaced about an outer surface of the main body; one or more ports spaced about the main body and forming a passage therethrough; and protrusions formed on an inner surface of the main body and extending in a generally perpendicular direction therefrom.

14 Claims, 23 Drawing Sheets

Related U.S. Application Data on Jul. 11, 2019, provisional application No. 62/845,540, filed on May 9, 2019.

(51) Int. Cl.
```
A61B 17/56    (2006.01)
A61B 34/10    (2016.01)
A61C 1/08     (2006.01)
A61C 9/00     (2006.01)
```

(52) U.S. Cl.
CPC ............ *A61C 1/084* (2013.01); *A61C 8/0028* (2013.01); *A61C 8/0069* (2013.01); *A61B 2017/568* (2013.01); *A61B 2034/102* (2016.02); *A61B 2034/105* (2016.02); *A61B 2034/108* (2016.02); *A61C 9/0046* (2013.01)

(56) References Cited

U.S. PATENT DOCUMENTS

| | | |
|---|---|---|
| 5,542,847 A | 8/1996 | Margulies |
| D655,816 S | 3/2012 | Llop et al. |
| 8,398,396 B2 | 3/2013 | Taormina |
| 8,419,426 B2 | 4/2013 | Paris et al. |
| 8,491,301 B2 | 7/2013 | Cho |
| 8,585,402 B2 | 11/2013 | Vogel et al. |
| 8,714,975 B2 | 5/2014 | Stumpel |
| 8,777,612 B2 | 7/2014 | Suttin et al. |
| 8,794,964 B2 | 8/2014 | Haber |
| 8,899,984 B2 | 12/2014 | Llop et al. |
| 8,956,158 B2 | 2/2015 | Schmälzle et al. |
| 9,004,919 B2 | 4/2015 | Llop |
| 9,226,801 B2 | 1/2016 | Groscurth et al. |
| 9,504,533 B2 | 11/2016 | Groscurth et al. |
| 9,687,327 B2 | 6/2017 | Prestipino |
| 9,693,834 B2 | 7/2017 | Llop |
| 9,763,757 B2 | 9/2017 | Llop et al. |
| 9,795,458 B2 | 10/2017 | Llop |
| 10,034,722 B2 | 7/2018 | Groscurth et al. |
| 10,213,275 B2 | 2/2019 | Groscurth et al. |
| 10,278,789 B2 | 5/2019 | Llop et al. |
| 10,307,226 B2 | 6/2019 | Llop et al. |
| 10,363,115 B2 | 7/2019 | Groscurth et al. |
| 10,398,530 B2 | 9/2019 | Llop et al. |
| 10,405,945 B2 | 9/2019 | Llop |
| 10,517,694 B2 | 12/2019 | Llop |
| 10,639,129 B2 | 5/2020 | Llop et al. |
| 11,160,639 B2 * | 11/2021 | Palmer ............... A61C 13/34 |
| 2008/0124672 A1 | 5/2008 | Sussman |
| 2009/0298008 A1 | 12/2009 | Groscurth et al. |
| 2010/0124731 A1 | 5/2010 | Groscurth et al. |
| 2011/0045431 A1 | 2/2011 | Groscurth et al. |
| 2011/0045432 A1 | 2/2011 | Groscurth et al. |
| 2011/0287381 A1 | 11/2011 | Sanders |
| 2012/0046914 A1 | 2/2012 | Gao |
| 2012/0191421 A1 | 7/2012 | Greenberg |
| 2013/0071811 A1 | 3/2013 | Groscurth et al. |
| 2014/0154638 A1 | 6/2014 | Kats |
| 2014/0272778 A1 | 9/2014 | Llop |
| 2014/0358246 A1 | 12/2014 | Levy et al. |
| 2015/0010881 A1 | 1/2015 | Llop |
| 2015/0056575 A1 | 2/2015 | Groscurth et al. |
| 2015/0272704 A1 | 10/2015 | Watson et al. |
| 2015/0272705 A1 | 10/2015 | Watson et al. |
| 2015/0308609 A1 | 10/2015 | Moens |
| 2016/0038255 A1 | 2/2016 | Llop |
| 2016/0106517 A1 | 4/2016 | Groscurth et al. |
| 2016/0278878 A1 | 9/2016 | Watson et al. |
| 2016/0331489 A1 | 11/2016 | Sanders et al. |
| 2016/0338714 A1 | 11/2016 | Schoenefeld et al. |
| 2016/0346062 A1 | 12/2016 | Lococo |
| 2016/0374778 A1 * | 12/2016 | Grobbee ............... A61C 13/01 433/74 |
| 2017/0112365 A1 | 4/2017 | Ostrovsky et al. |
| 2017/0112591 A1 | 4/2017 | Llop |
| 2017/0112592 A1 | 4/2017 | Groscurth et al. |
| 2017/0209235 A1 * | 7/2017 | Fisker ............... A61C 1/085 |
| 2017/0265963 A1 * | 9/2017 | Yau ............... A61C 1/084 |
| 2017/0290646 A1 | 10/2017 | Prestipino |
| 2018/0036103 A1 | 2/2018 | Llop |
| 2018/0221109 A1 | 8/2018 | Chung et al. |
| 2018/0263727 A1 | 9/2018 | Pellerito |
| 2018/0333229 A1 | 11/2018 | Watson |
| 2019/0000590 A1 | 1/2019 | Groscurth et al. |
| 2019/0038378 A1 | 2/2019 | Nulty |
| 2019/0209267 A1 * | 7/2019 | Massoels ............... A61C 1/082 |
| 2019/0216577 A1 * | 7/2019 | Llop ............... A61C 8/0027 |
| 2019/0216581 A1 | 7/2019 | Watson |
| 2019/0216851 A1 | 7/2019 | Xiao et al. |
| 2019/0223988 A1 * | 7/2019 | Palmer ............... A61C 1/084 |
| 2019/0262107 A1 | 8/2019 | Jusuf et al. |
| 2019/0314114 A1 | 10/2019 | Watson |
| 2019/0380783 A1 | 12/2019 | Gemon et al. |
| 2019/0388184 A1 | 12/2019 | Jusuf et al. |
| 2019/0388185 A1 | 12/2019 | Jusuf et al. |
| 2020/0015934 A1 | 1/2020 | Llop et al. |
| 2020/0146770 A1 | 5/2020 | Schmälzle |
| 2020/0155271 A1 | 5/2020 | Groscurth et al. |
| 2020/0163740 A1 | 5/2020 | Llop |
| 2020/0352736 A1 | 11/2020 | Van Rensburg et al. |
| 2021/0369402 A1 | 12/2021 | Jusuf et al. |
| 2021/0369407 A1 | 12/2021 | Groscurth et al. |
| 2022/0031364 A1 | 2/2022 | Frey et al. |
| 2022/0071671 A1 | 3/2022 | Little et al. |
| 2022/0079709 A1 | 3/2022 | Van Rensburg et al. |
| 2022/0362023 A1 | 11/2022 | Toranto |

FOREIGN PATENT DOCUMENTS

| | | | |
|---|---|---|---|
| EP | 2229909 A1 | 9/2010 | |
| FR | 2942953 A1 | 9/2010 | |
| KR | 101457011 B1 * | 11/2014 | ............ A61B 17/16 |
| KR | 2019-0041668 A | 4/2019 | |
| WO | 2009115617 A1 | 9/2009 | |
| WO | 2010061124 A1 | 6/2010 | |
| WO | 2014/072919 A1 | 5/2014 | |
| WO | 2016012223 A1 | 1/2016 | |
| WO | 2017/069797 A1 | 4/2017 | |
| WO | 2017/143107 A1 | 8/2017 | |
| WO | 2017/203419 A1 | 11/2017 | |
| WO | 2018/213817 A1 | 11/2018 | |
| WO | 2019/144163 A1 | 7/2019 | |
| WO | 2019240691 A1 | 12/2019 | |

OTHER PUBLICATIONS

Cowellmedi Co. Ltd., "Cowell® Direct Surgical Guide Kit", available on web https://pdf.medicalexpo.com/pdf/cowellmedi/cowell-direct-surgical-guide-kit/102495-178350-_3.html, retrieved from web on Jun. 29, 2020, 2019, 13 pages.

Trobough et al., "Surgical Guide Techniques for Dental Implant Placement", Decisions in Dentistry, available on https://decisionsindentistry.com/article/surgical-guide-techniques-for-dental-implant-placement/, retrieved from web on Jun. 29, 2020, Jul. 24, 2018, 11 pages.

Alzoubi et al., "Bone Reduction to Facilitate Immediate Implant Placement and Loading Using CAD/CAM Surgical Guides for Patients with Terminal Dentition", Journal of Oral Implantology, 2016, 36 pages.

IBUR Early Stackable, "Surgical Guide Options", 2016, 2017, 1 page.

IBUR Early Stackable, "Mandible Virtually Planned Surgery", 2016, 2017, 4 pages.

Charette et al., "Cone Beam Computed Tomogrpahy Imaging as a Primary Diagnostic Tool for Computer-Guided Surgery", The Journal of Prosthetic Dentistry, 2016, 9 pages.

Hu et al., "Computer-Designed Surgical Guide Template", Medicine, 2017, 6 pages.

Pikos et al., "Guided Full-Arch Immediate-Function Treatment Modality for the Edentulous and Terminal Dentition Patient", nSequence Compendium, 2015, 6 pages, vol. 36, Issue 2.

(56) References Cited

OTHER PUBLICATIONS

Zhang et al., "Accuracy of Virtual Surgical Planning in Two-Jaw Orthognathic Surgery: Comparison of Planned and Actual Results", Oral and Maxillofacial Surgery, 2016, 9 pages.

Wong, "Predictable Immediate Implant Prosthetics Using Guided Surgery and Guided Prosthetics: A Case Report", Oral Health Group, 2016, available on https://www.oralhealthgroup.com/features/1003918999/, retrieved from web on Aug. 10, 2021, 21 pages.

Salama et al., "The Scalloped Guide: A Proof-of-Concept Technique for a Digitally Streamlined, Pink-Free Full-Arch Implant Protocol", The International Journal of Periodontics & Restorative Dentistry, 2018, vol. 38, No. 6, 9 pages.

\* cited by examiner

TISSUE BORNE STACKABLE FOUNDATION GUIDE AND METHOD OF MAKING AND USING SAME

RELATED APPLICATIONS

This application is related and claims priority to U.S. Provisional Patent Application Nos. 62/845,540, entitled "Tissue Borne Stackable Foundation Guide" filed on May 9, 2019; 62/872,829, entitled "Unilateral Key Fixation (UKF) System, Device, and Methods for Making and Using Same" filed on Jul. 11, 2019; and 62/912,821, entitled "Tissue Borne Fixation (TBF) System, Device, and Methods of Making and Using Same" filed on Oct. 9, 2019, the applications of which are incorporate herein by reference in their entirety.

TECHNICAL FIELD

The presently disclosed subject matter relates generally to a dental guide and more particularly to a unilateral tissue borne stackable foundation guide with tissue thickness seating indicators.

BACKGROUND

In currently available dental surgical guides and methods, when a dental practitioner sets a guide directly on a patient's gum tissue for a procedure, such as dental implant surgery, the practitioner uses traditional mechanical torque wrench/ value based off resistance force to measure depth and tightness of the guide's screws to seat the guide. However, these values can vary greatly depending on a particular patient's bone thickness, density, etc., and therefore does not effectively account for the patient's actual gum tissue thickness, swelling, location, etc. Consequently, it is very common for a dental practitioner to overtighten the guide screws when seating the guide. Overtightening the guide screws can result in the patient's gum tissue becoming overly compressed by the guide. Compression of the gum tissue under the guide causes the blood flow to be cut off and can cause necrosis, killing or permanently damage the patient's gum tissue.

In addition, many of the current guides require the guide to be seated directly on the patient's bone (bone borne) or "float" off the bone, and thereby require reflection or cutback of the patient's gum tissue. The procedure for reflection or cutback of the patient's gum tissue adds additional procedure time, complexity, and patient risk. Reflection or cutback of the patient's gum tissue is a very invasive, and can increase the patient's discomfort during and after the procedure, overall recovery time, and potential for complications.

Therefore, there is a need for a way to prevent practitioners from over tightening guide screws when seating a guide and damaging a patient's gum tissue. There is also a need to provide for a less invasive, faster, and safer surgery with overall better patient care and recovery.

SUMMARY

In one embodiment, a tissue borne stackable foundation guide is provided. The foundation guide may include a main body; first connectors formed on and spaced about an outer surface of the main body; one or more ports spaced about the main body and forming a passage therethrough; and protrusions formed on an inner surface of the main body and extending in a generally perpendicular direction therefrom. The protrusions may include conical shaped bodies tapering to a point at a distal end. The one or more of the protrusions may be disposed proximate to the one or more ports. The protrusions may be localized in groups proximal to one or more of the one or more ports. The protrusions comprise a length, such that when the foundation guide is seated on a patient's gum tissue, the distal most ends of the protrusions do not engage underlying bone of the patient. The one or more ports may be configured to receive a fixation mechanism therethrough, and wherein the fixation mechanism may be configured for anchoring the foundation guide to a maxillary or mandibular bone of a patient. The fixation mechanism may include at least one of a fixation pin and screw. The first connectors may each include a first coupling hole, wherein the first coupling hole may form a passageway through the first connector that is substantially perpendicular to a length of the first connector. The first connectors may include connection sleeves, the connection sleeves may include a lengthwise passageway therethrough. The main body may include a generally curved shape in a general shape of a gum line of a patient. The foundation guide may further include a stackable component. The stackable component may include a component body; and second connectors spaced about an outer edge of the component body, wherein the second connectors may be configured to engage with the first connectors. The second connectors may each may include a second coupling hole, wherein the second coupling hole may form a passageway through the second connectors that may be substantially perpendicular to a length of the second connector. The first connectors and second connectors may be configured such that when engaged the second connectors seat into voids formed in corresponding ones of the first connectors, and wherein when the second connectors are seated into corresponding first connectors, the second coupling holes may be aligned with first coupling holes formed in corresponding first connectors. The stackable component may be secured to the foundation guide via one or more coupling mechanisms inserted through the aligned first and second coupling holes. The stackable guide may be configured to facilitate a dental procedure. The stackable guide may further include one of a surgical component and/or a prosthetic component formed thereon. The surgical component may include a surgical drill guide.

In another embodiment, a method of making a tissue borne stackable foundation guide is provided. The method of making the tissue borne stackable foundation guide may include, modeling a patient's mouth; planning the desired surgical procedure; designing and fabricating the foundation guide; designing and fabricating one or more desired stackable components; and wherein the designed foundation guide may include a main body portion, the main body portion may include protrusions formed on an inner surface of the main body and extending in a generally perpendicular direction therefrom, wherein the protrusions, when the foundation guide is seated on a patient's gum tissue, are configured to pierce a patient's gum tissue to a depth slightly less than or equal to a thickness of the patient's gum tissue.

In yet another embodiment, a method of using a tissue borne stackable foundation guide is provided. The method of using the tissue borne stackable foundation guide may include, positioning a foundation guide in a patient's oral cavity; fixating the foundation guide to the patient's gum tissues; positioning and securing a desired stackable component to the foundation guide; conducting a planned procedure; and wherein the foundation guide may include a main body portion, the main body portion may include protrusions formed on an inner surface of the main body and extending in a generally perpendicular direction therefrom, wherein the protrusions, when the foundation guide is seated on a patient's gum tissue, are configured to pierce a patient's gum tissue to a depth slightly less than or equal to a thickness of the patient's gum tissue.

In still yet another embodiment, a dental device is provided. The dental device may include a main body configured for unilateral seating to a buccal mucosa of a patient; and protrusions formed on an inner surface of the main body and extending in a generally perpendicular direction therefrom, wherein the protrusions, when the main body is seated to the buccal mucosa of the patient, may be configured to pierce a patient's gum tissue to a depth slightly less than or equal to a thickness of the patient's gum tissue.

BRIEF DESCRIPTION OF THE DRAWINGS

Figure 1:
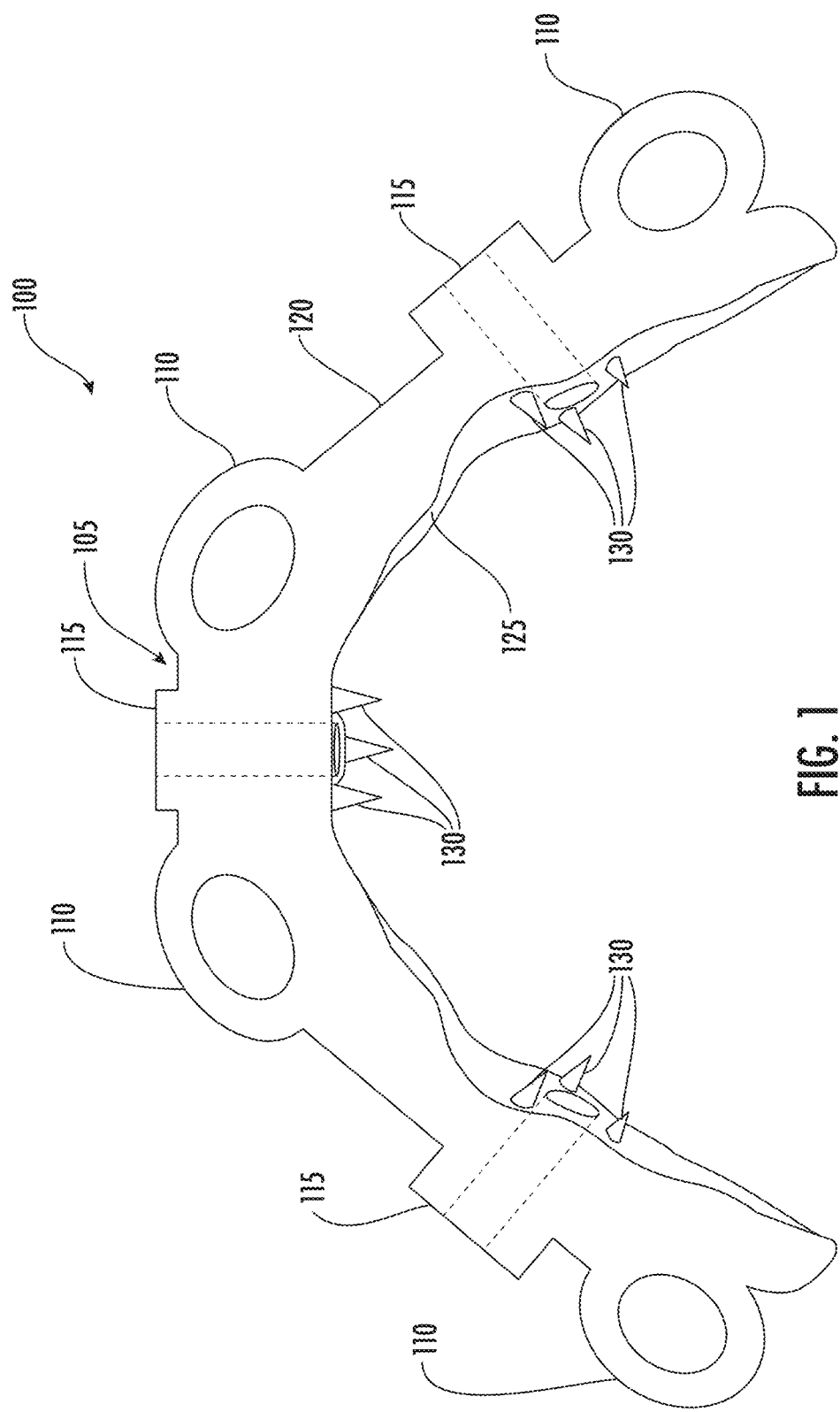
Figure 2:
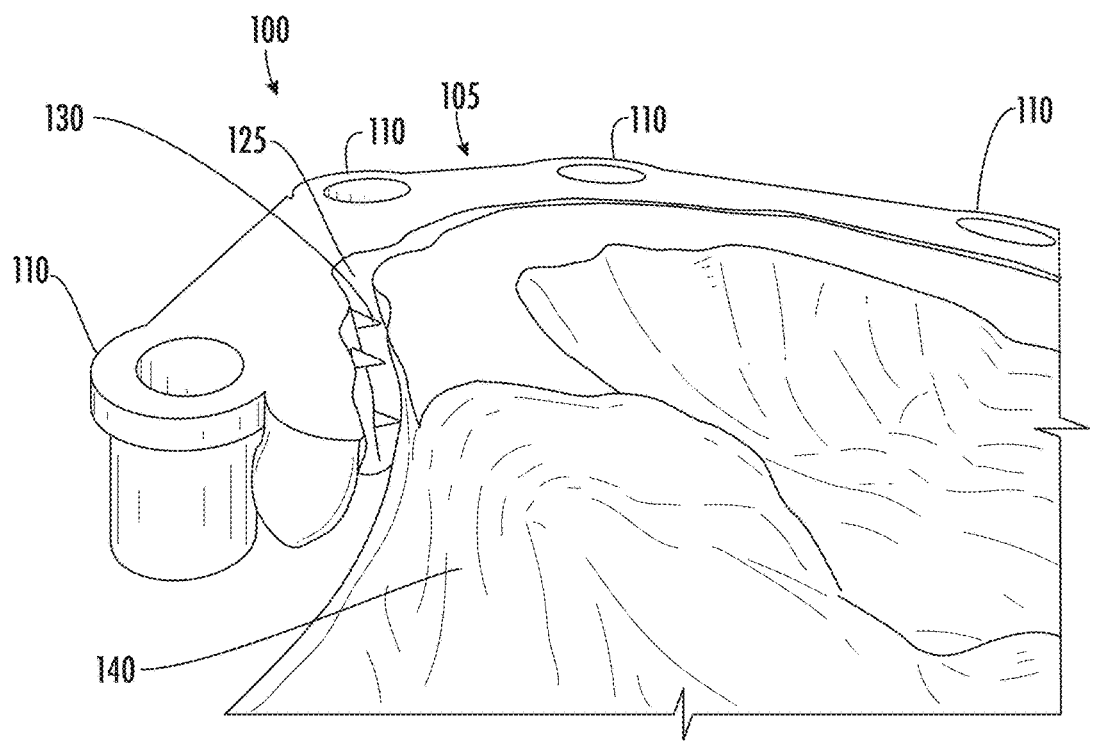
Figure 3:
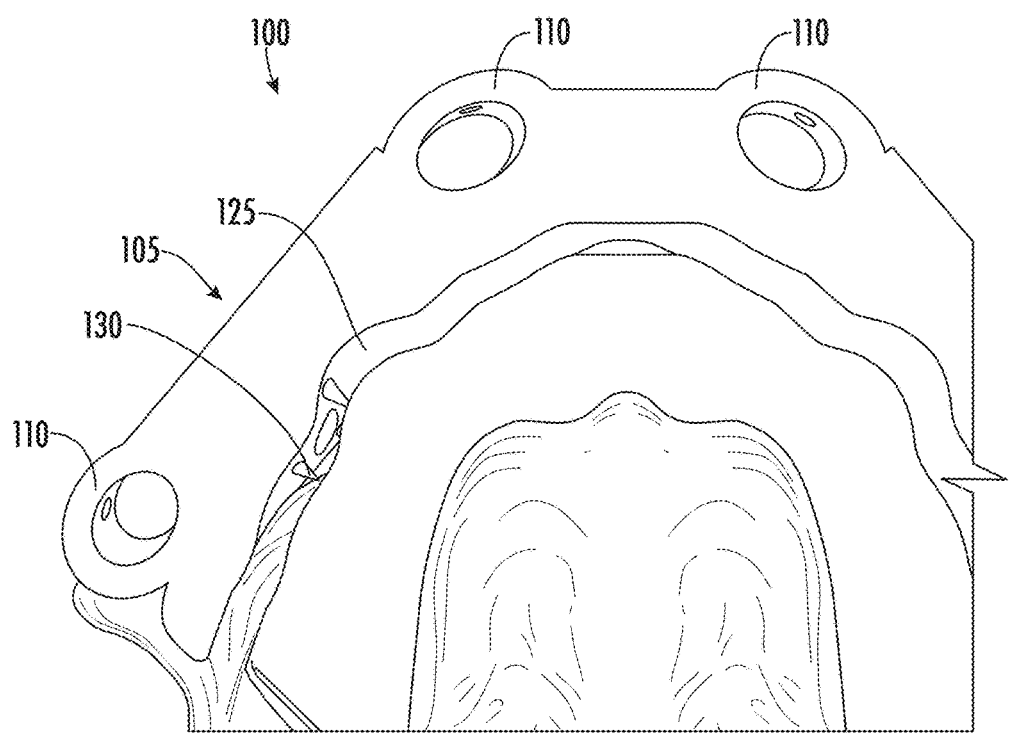
Figure 4:
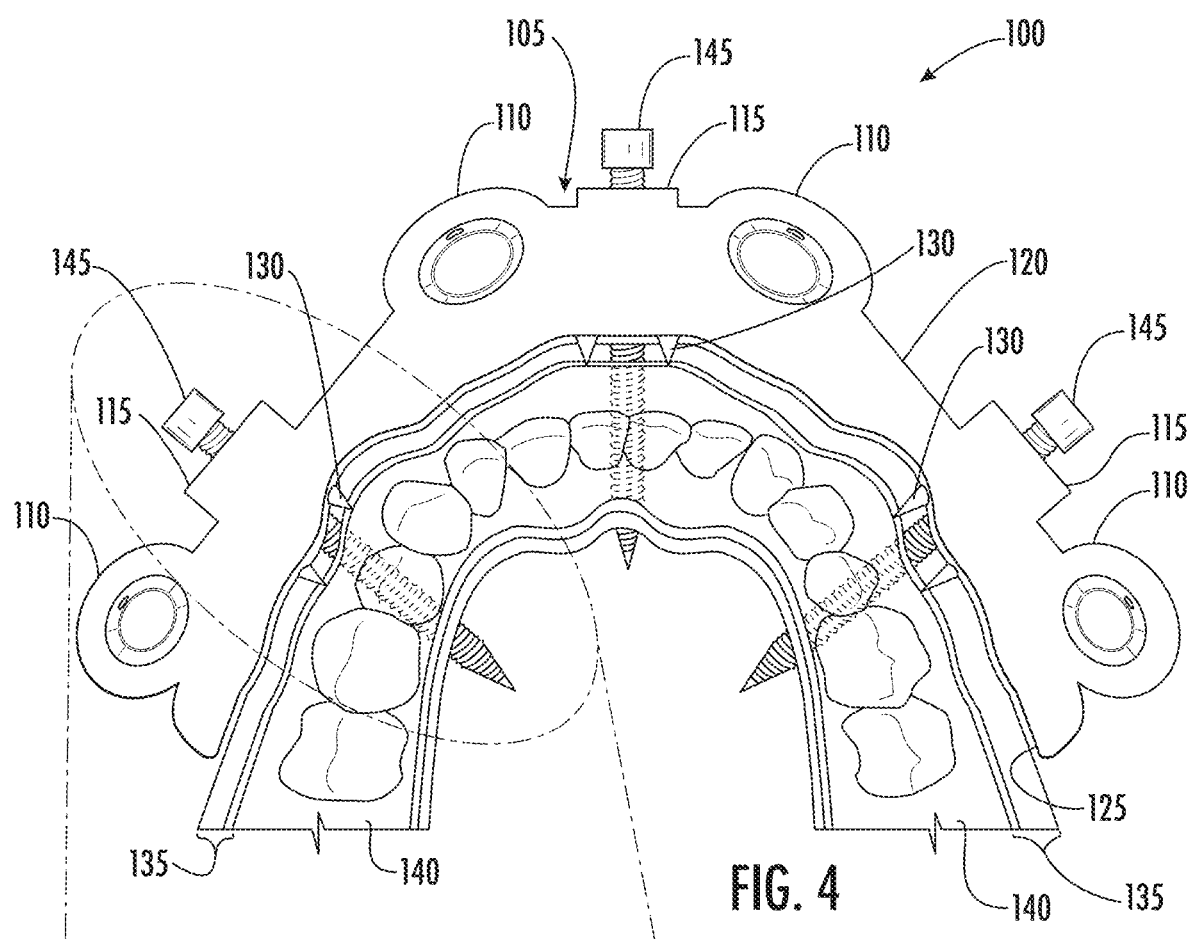
Figure 5:
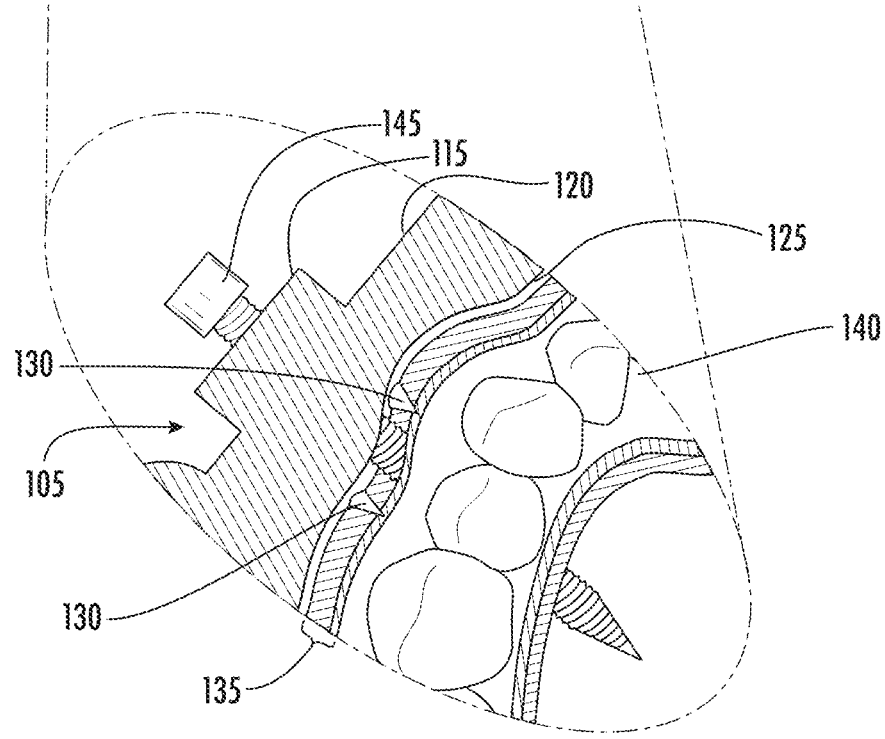
Figure 6:
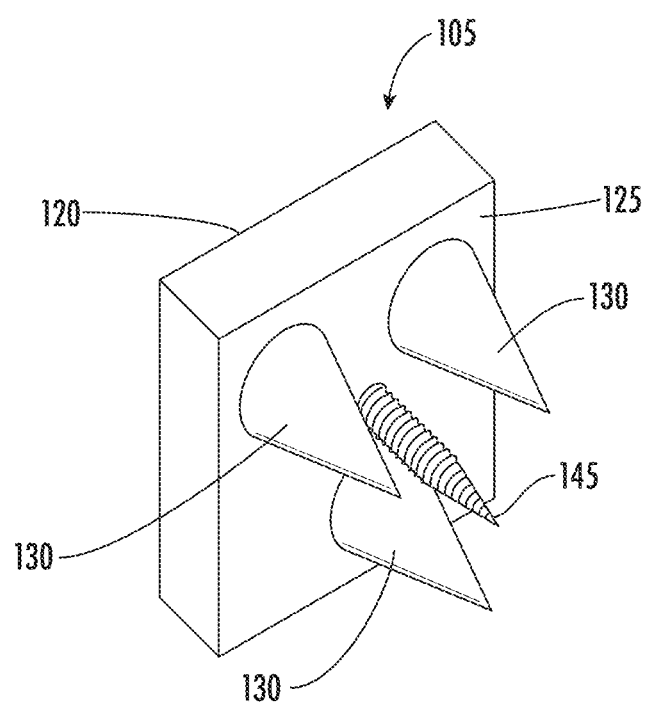
Figure 7:
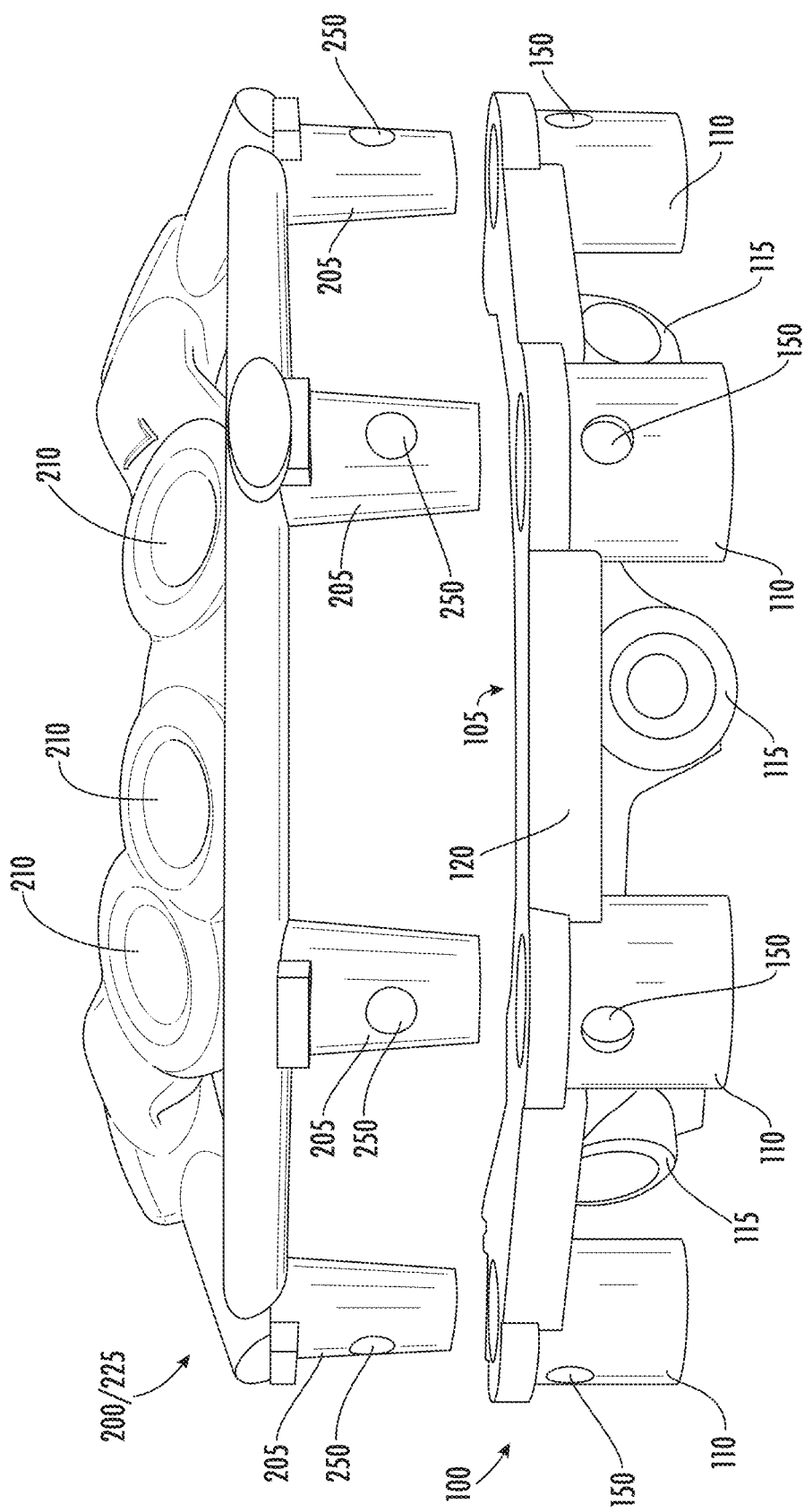
Figure 8:
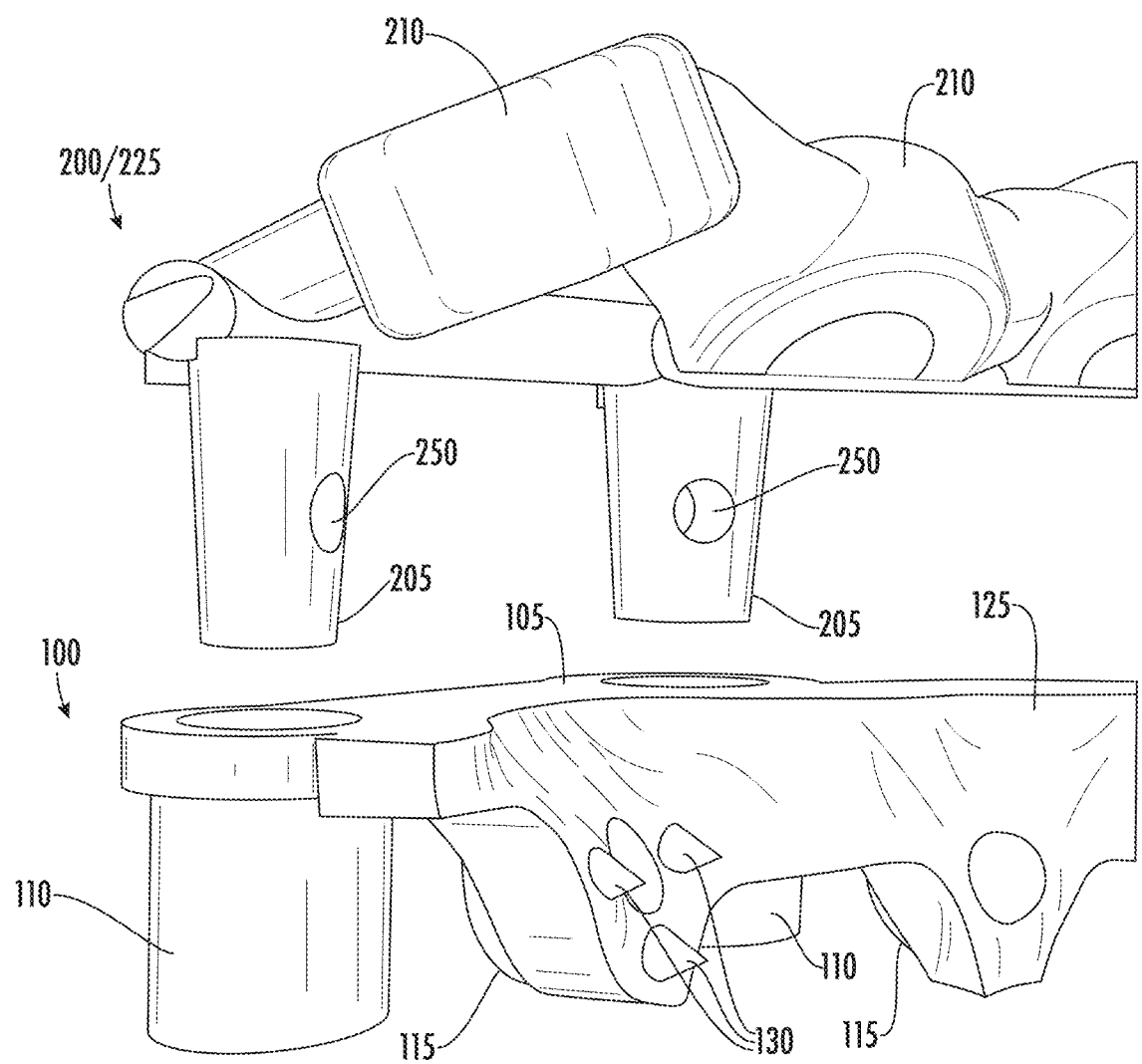
Figure 9:
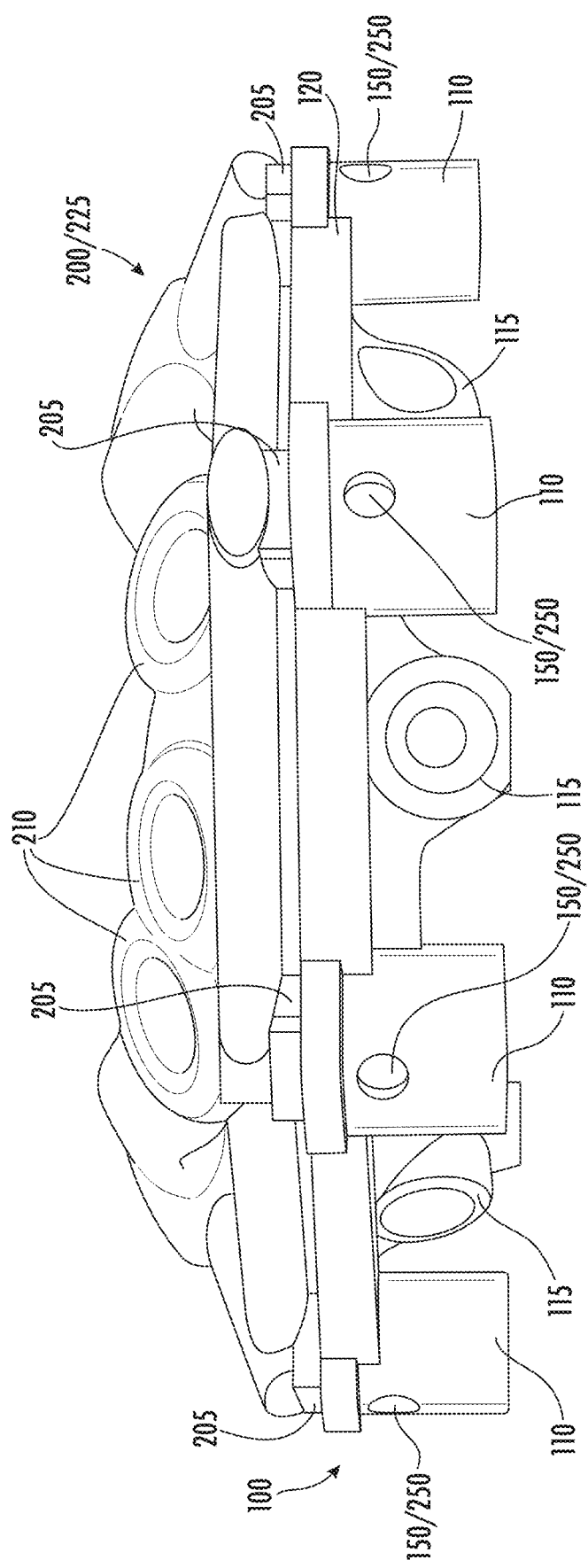
Figure 10:
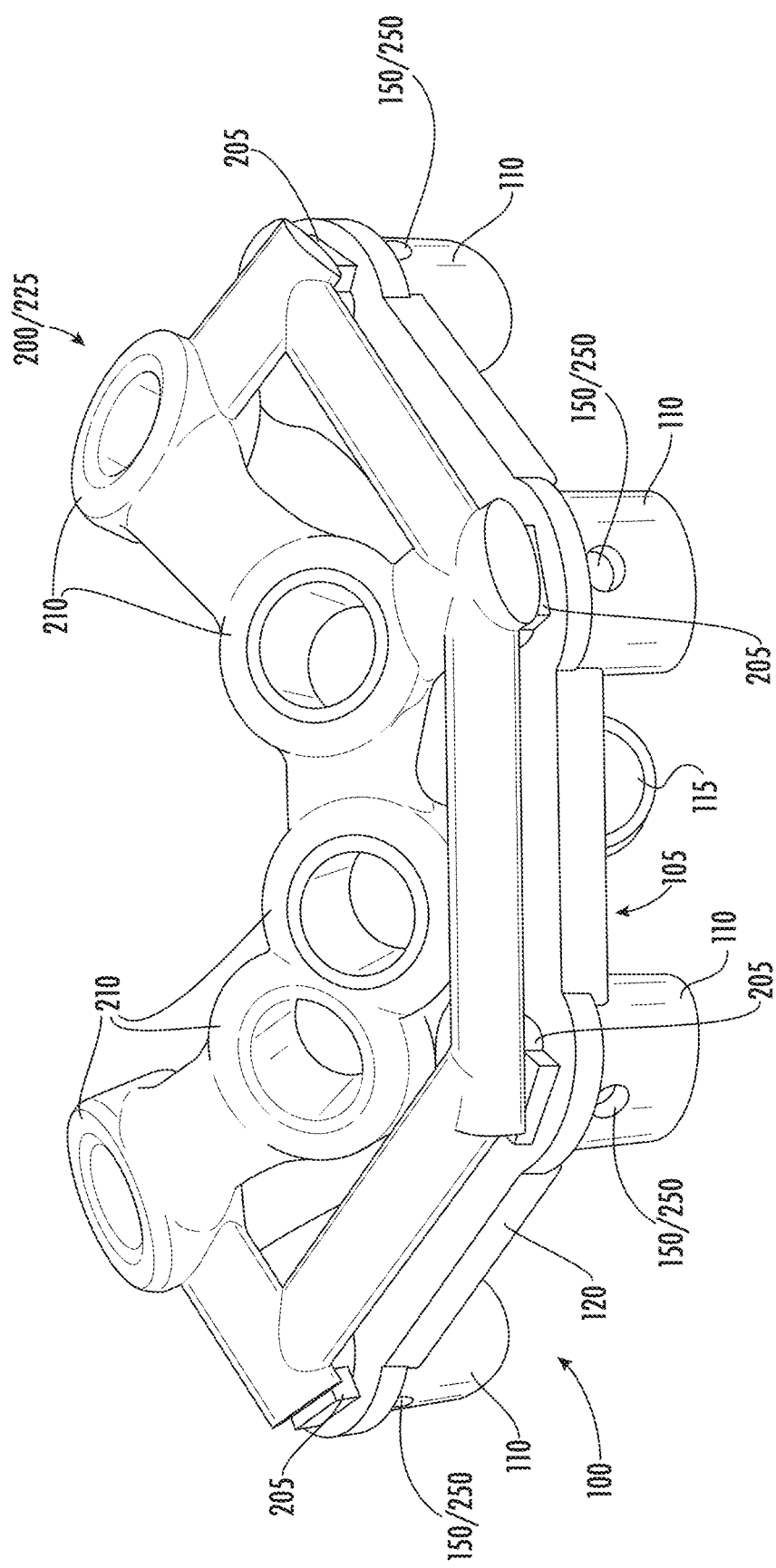
Figure 11:
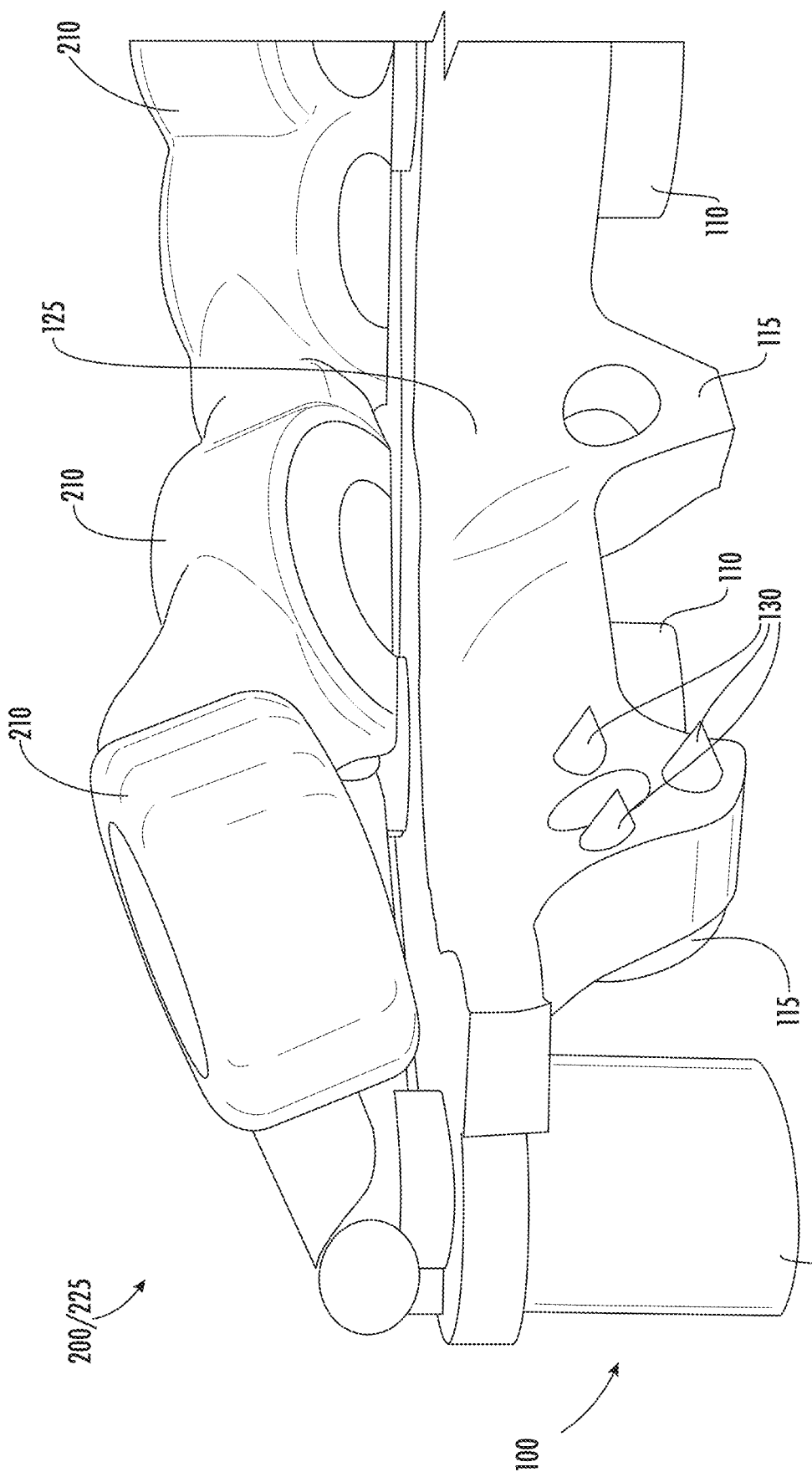
Figure 12:
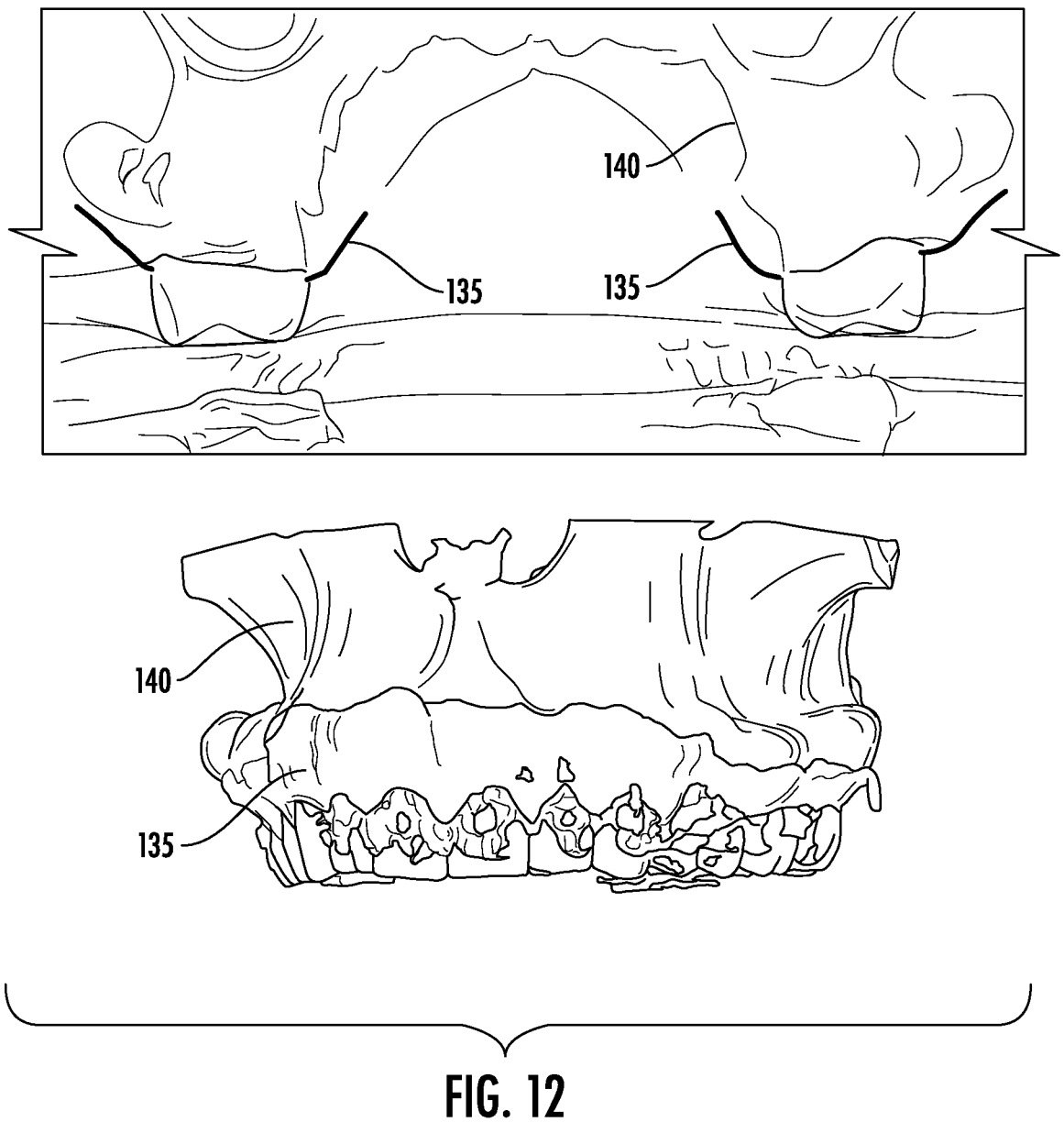
Figure 13:
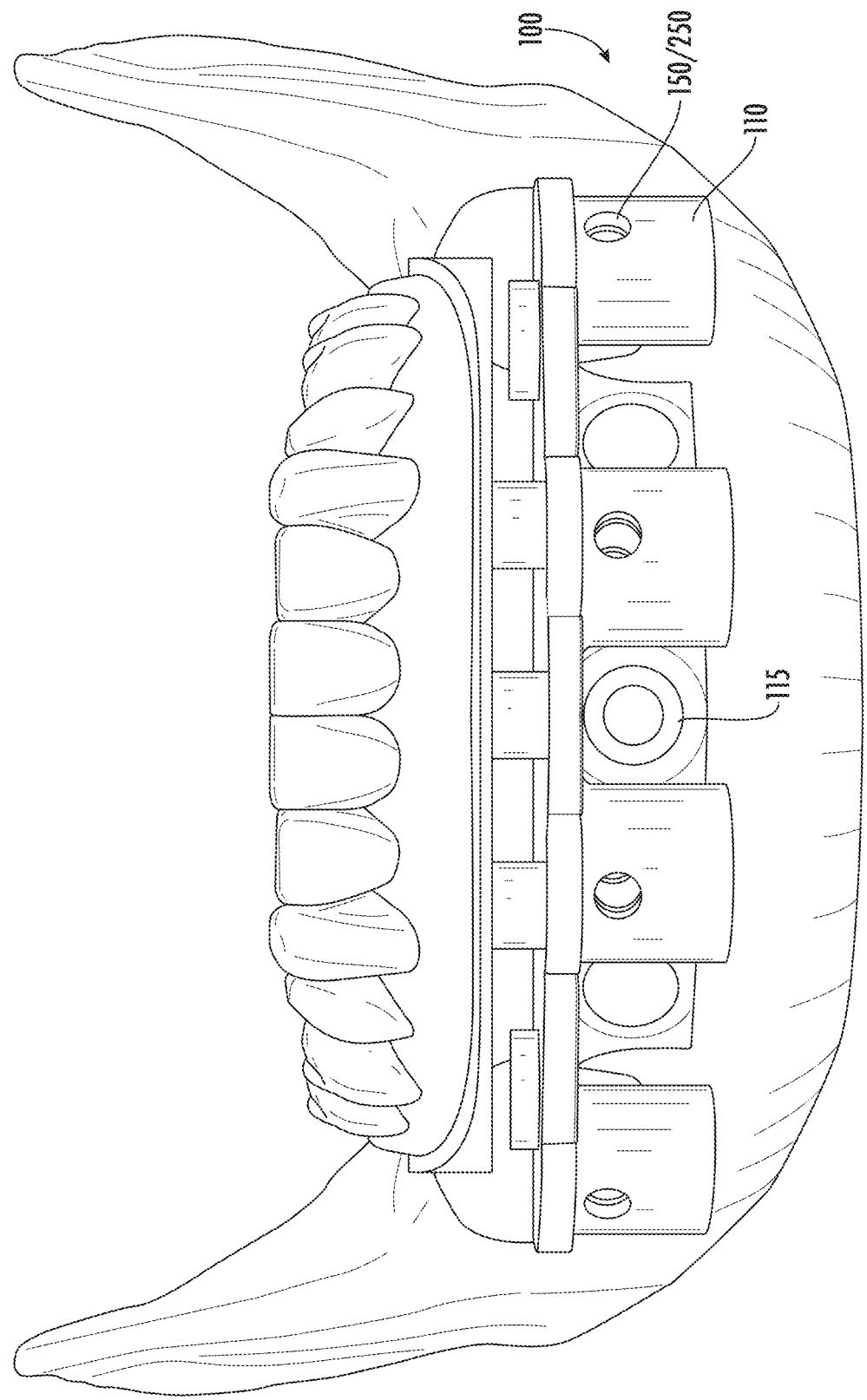
Figure 14:
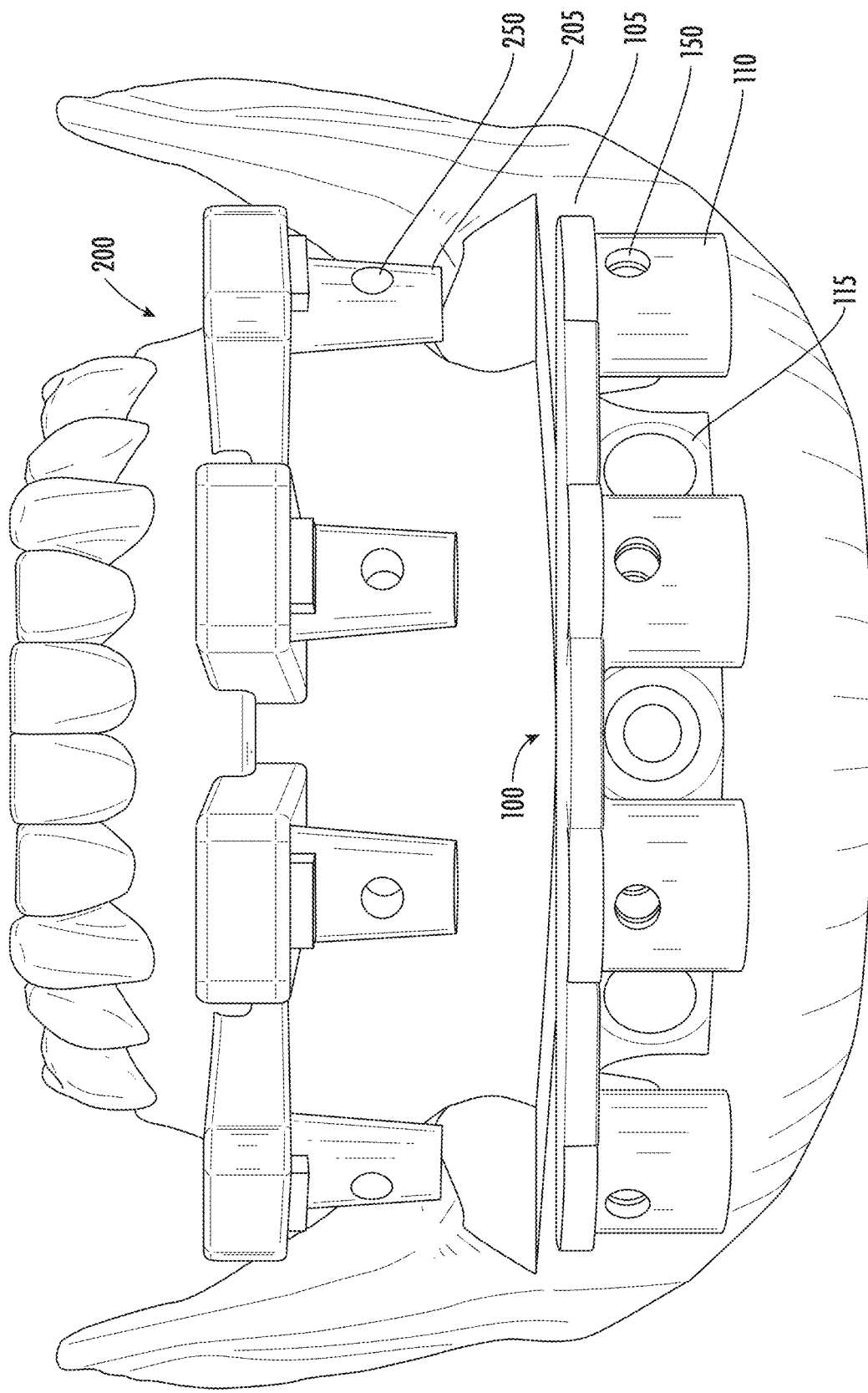
Figure 15:
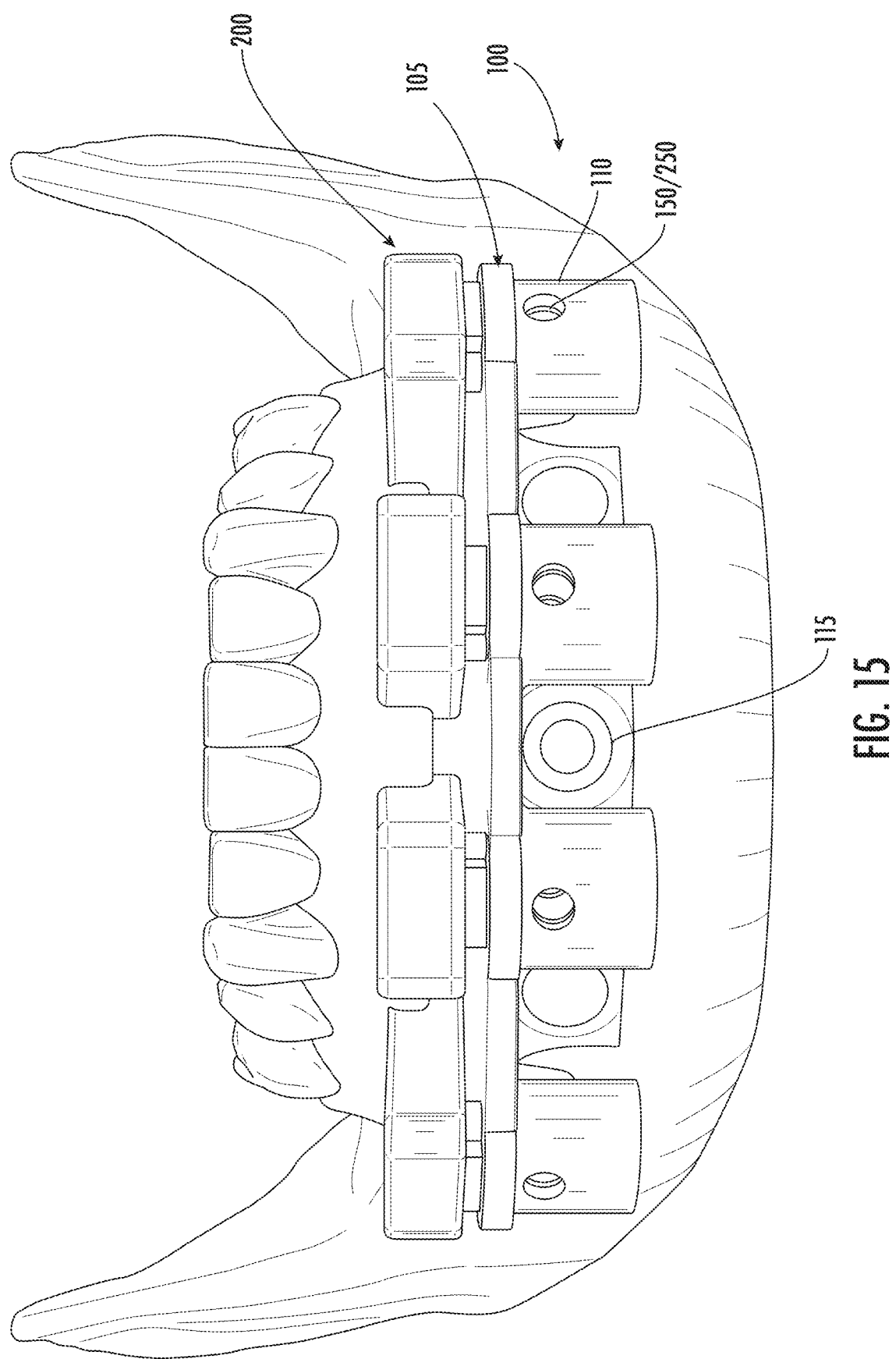
Figure 16:
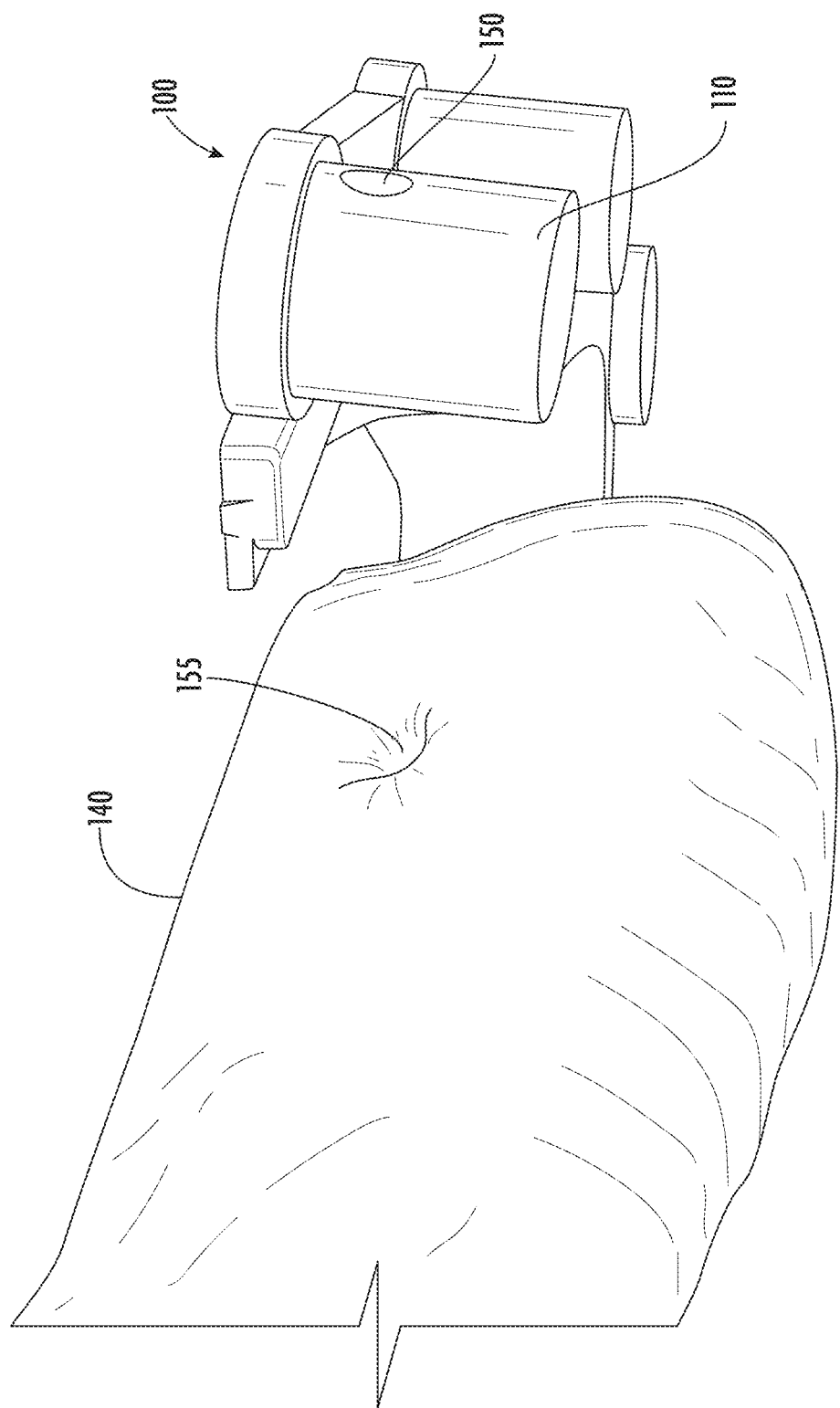
Figure 17:
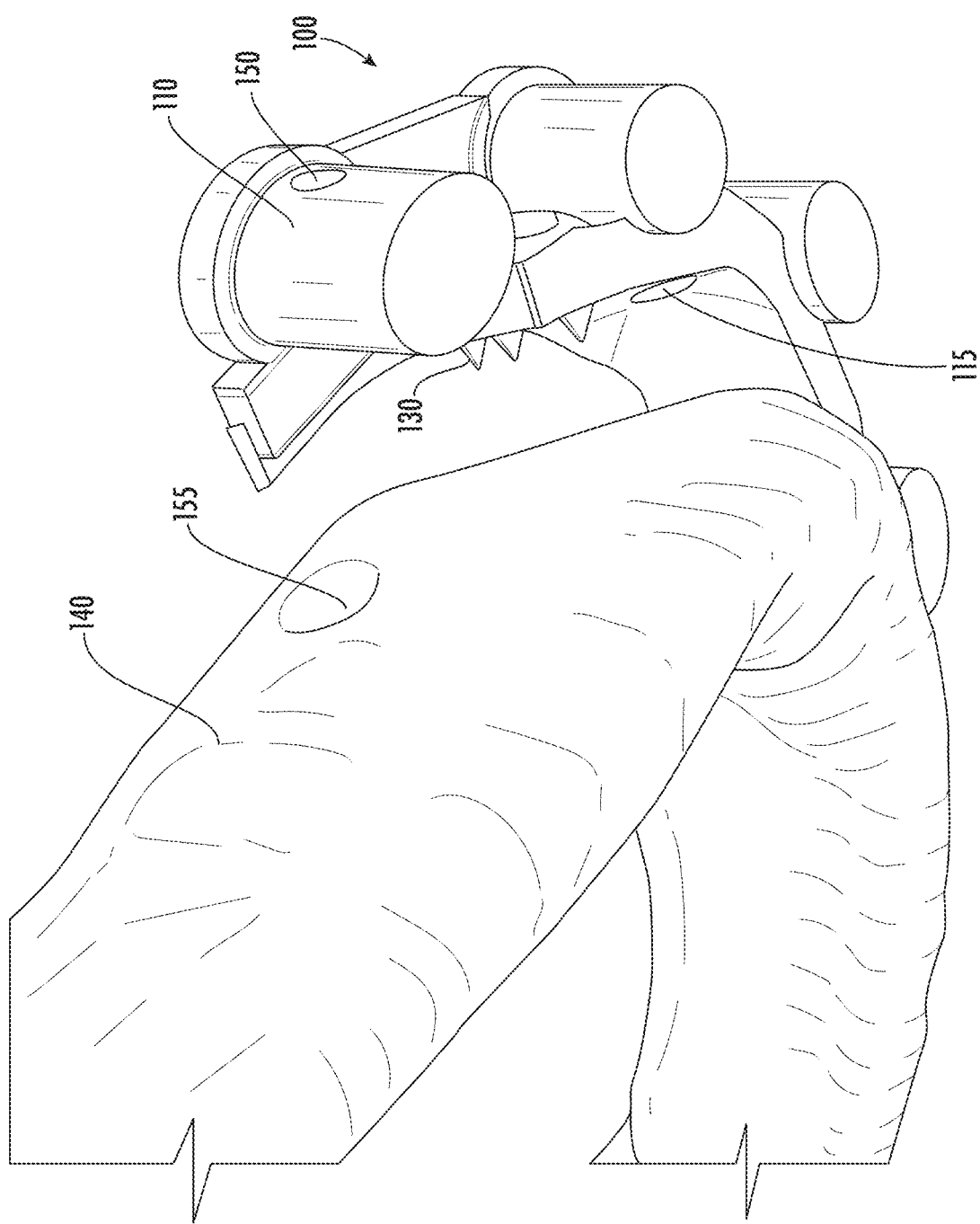
Figure 18:
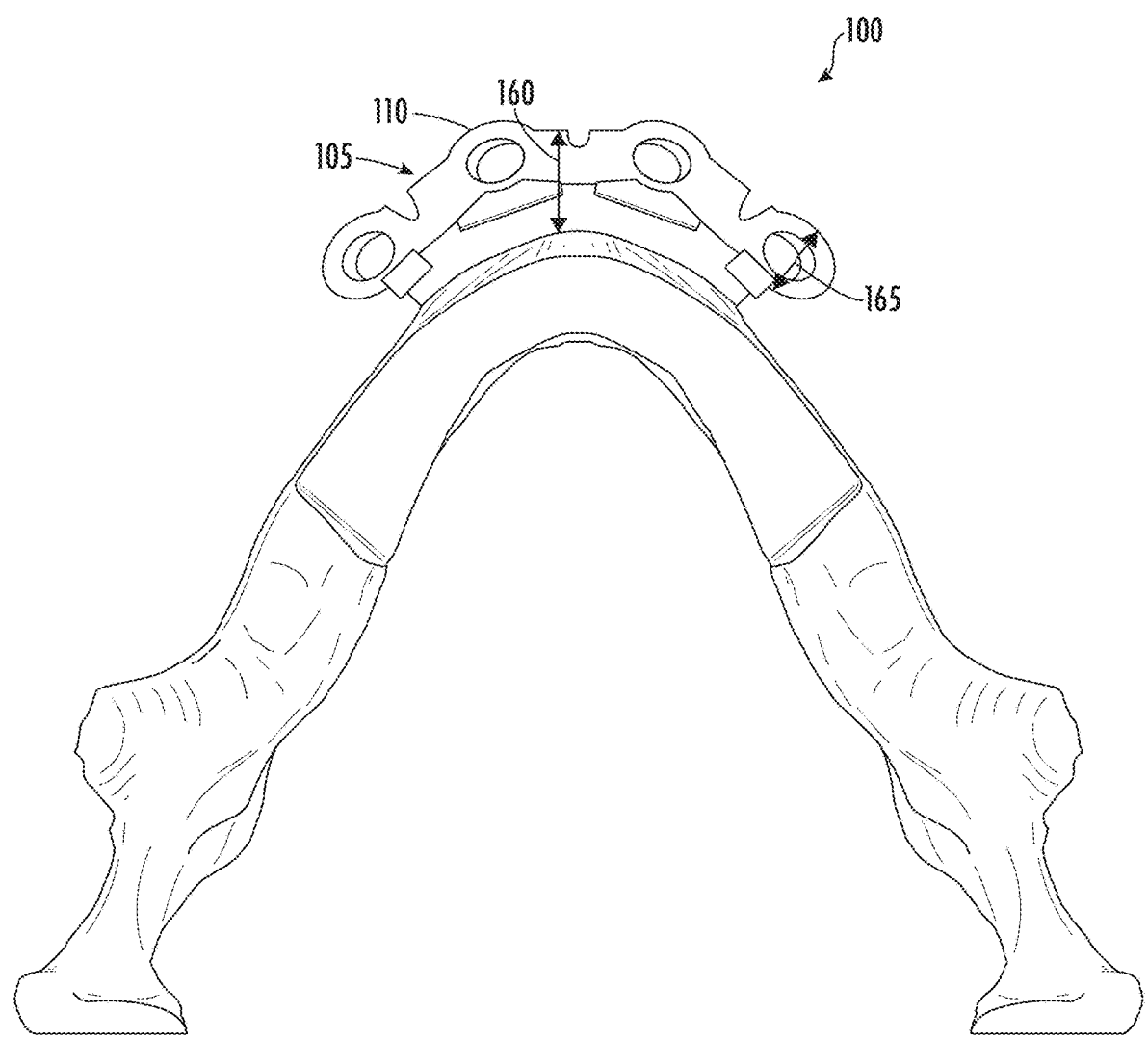
Figure 19:
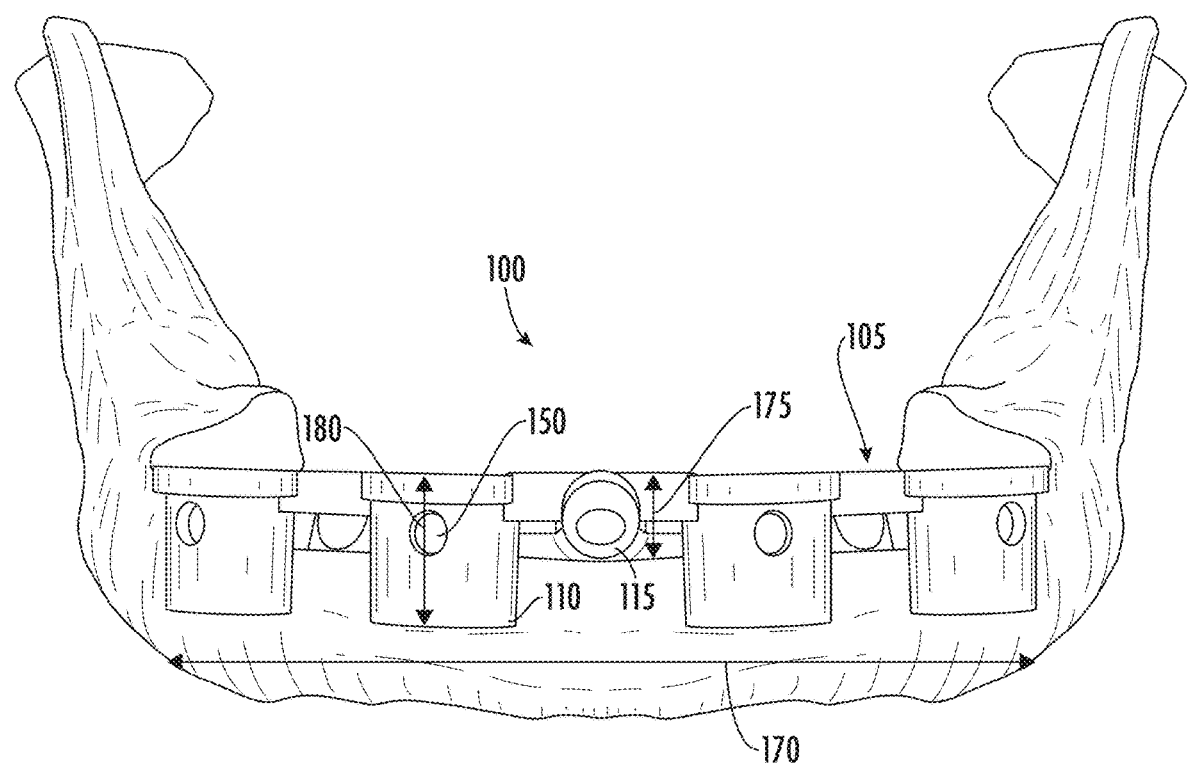
Figure 20:
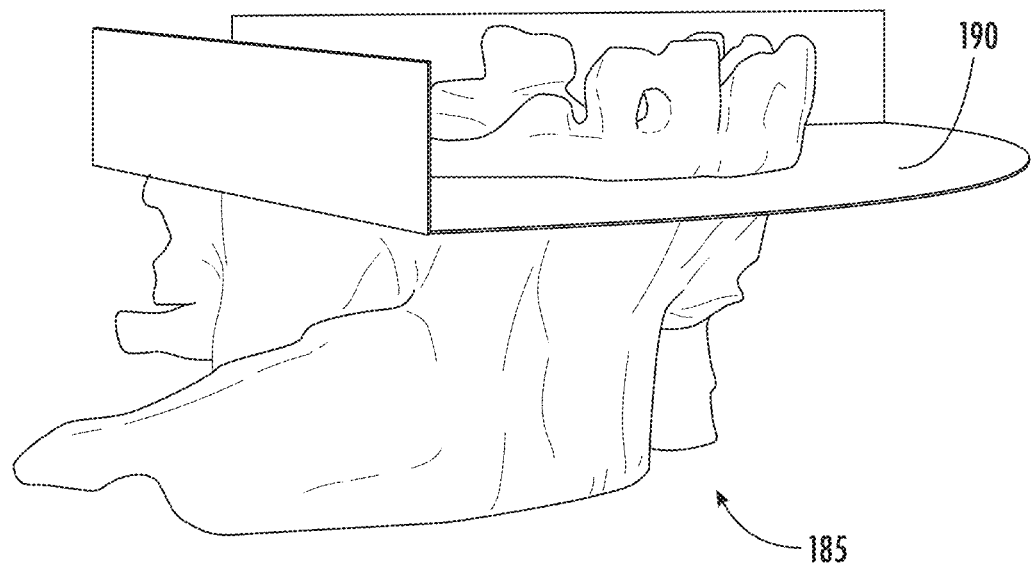
Figure 21:
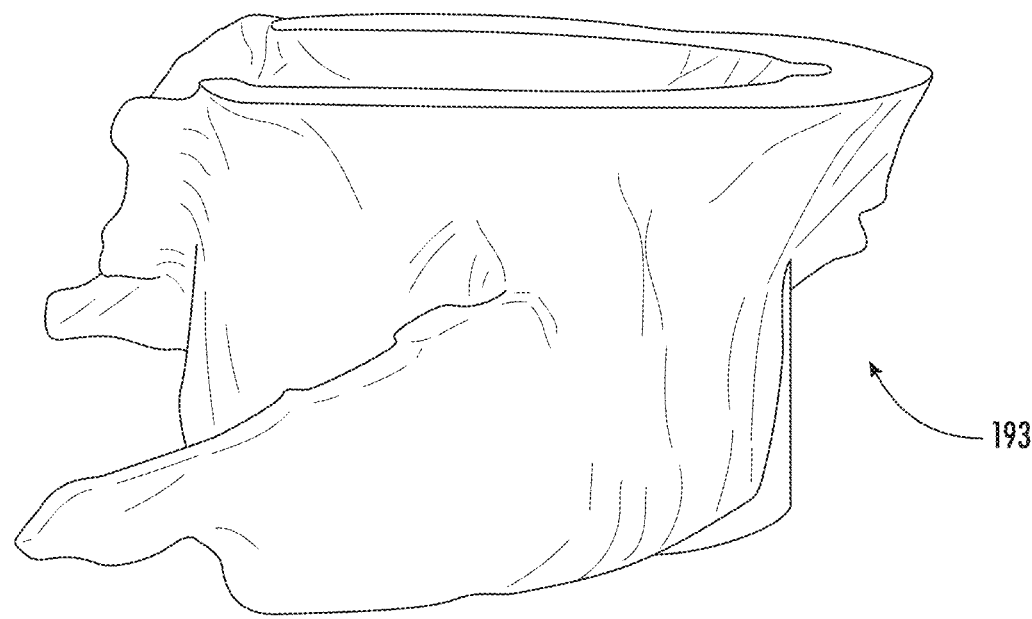
Figure 22:
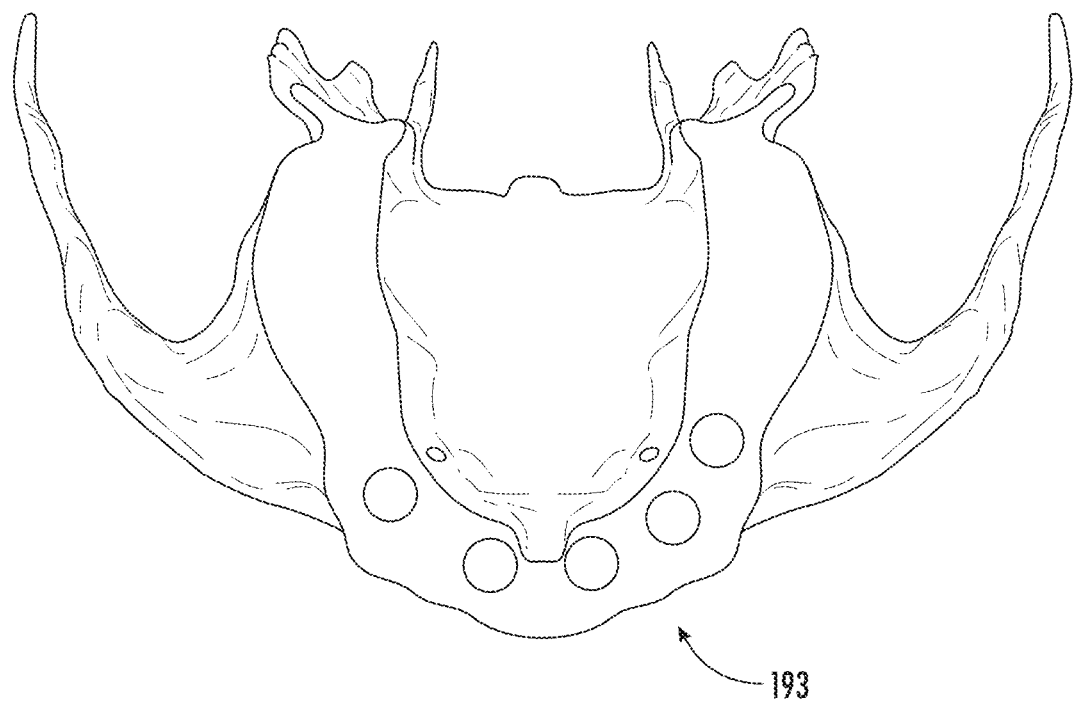
Figure 23:
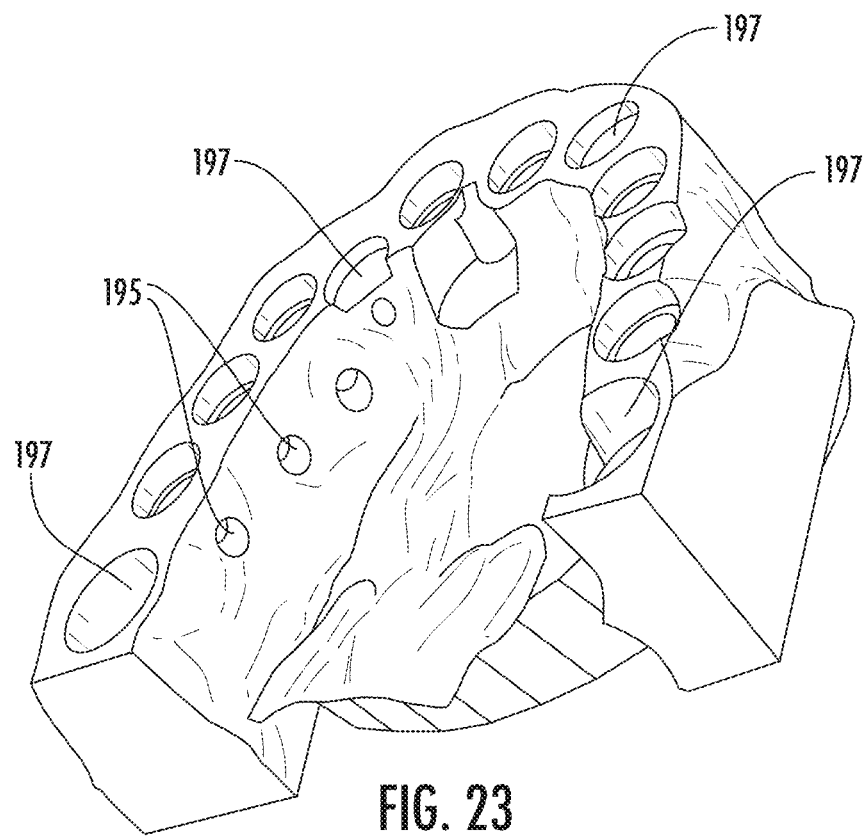
Figure 24:
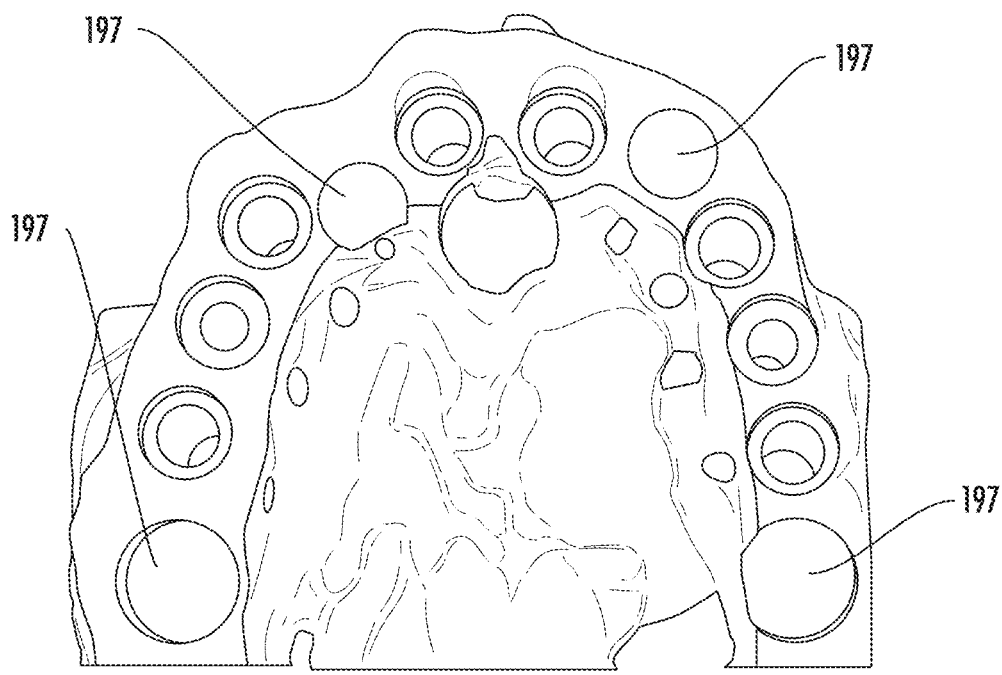
Figure 25:
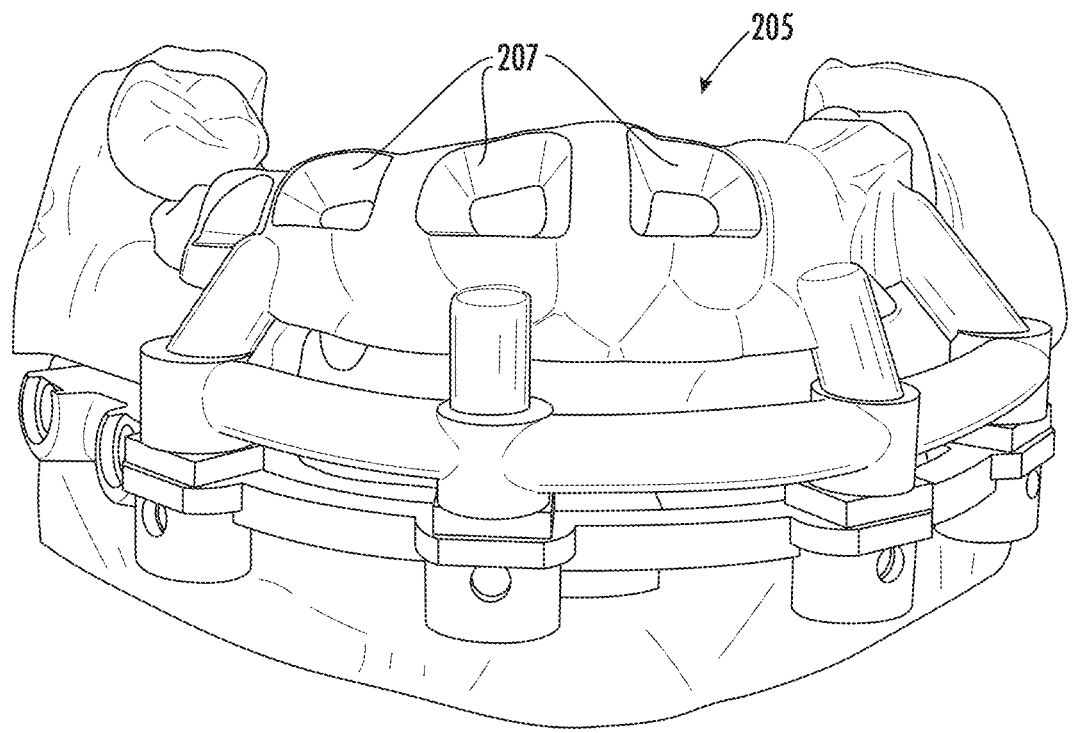
Figure 26:
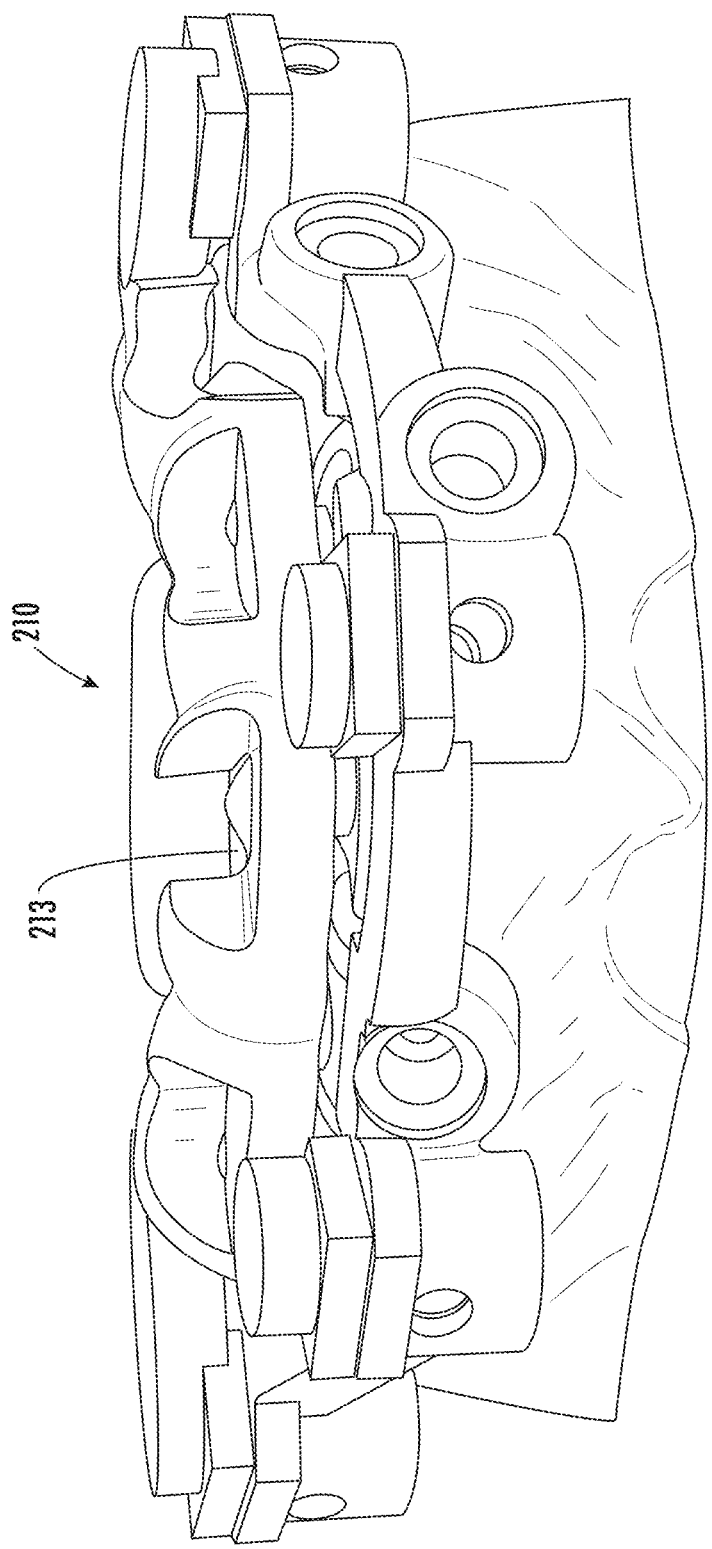
Figure 27:
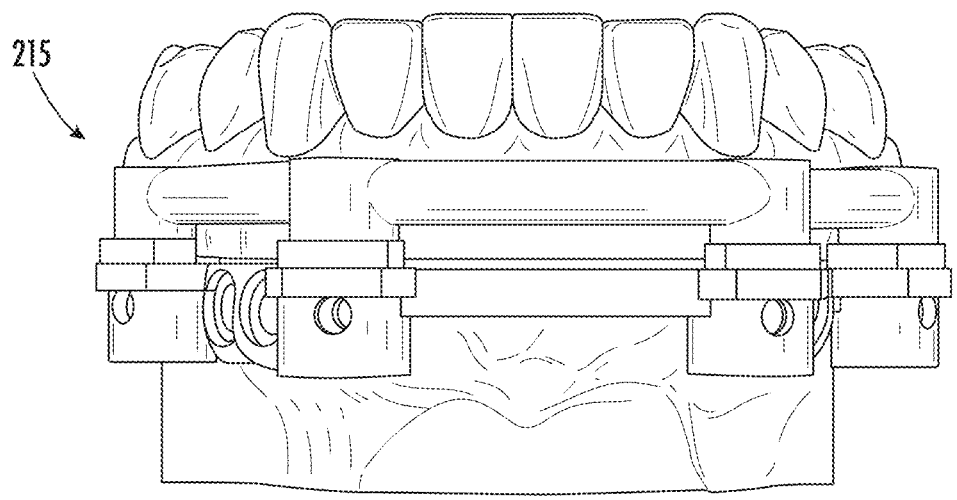
Figure 28:
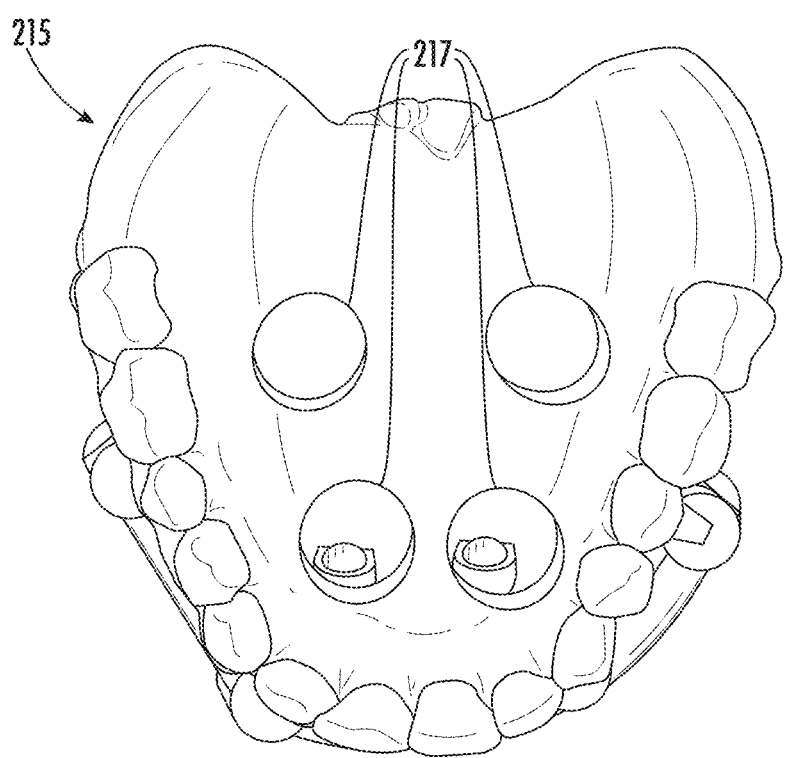
Figure 29:
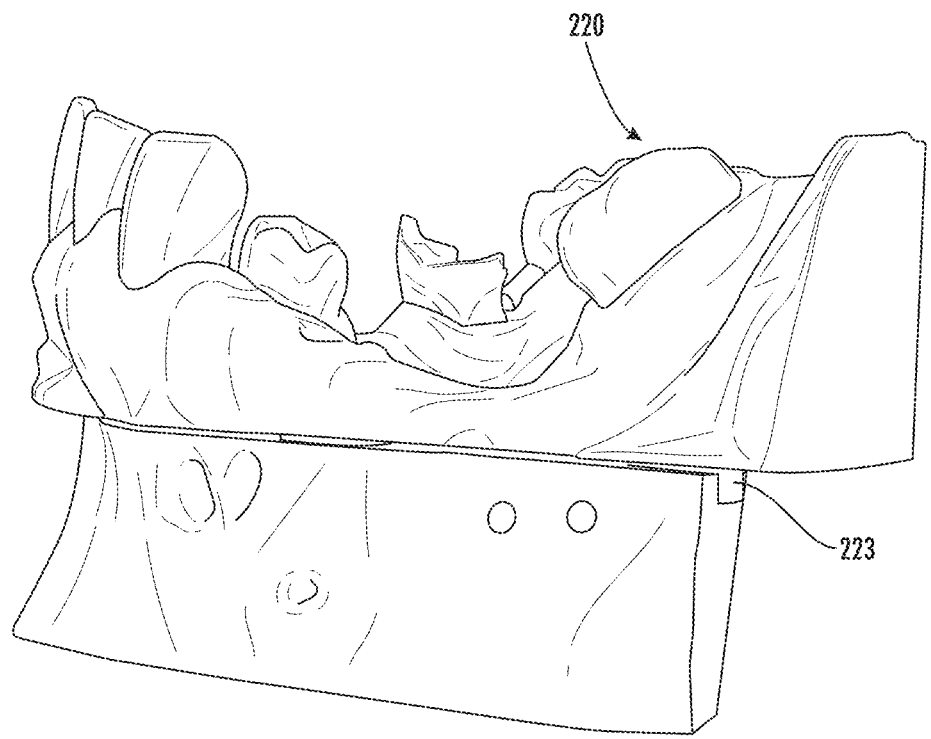

Having thus described the presently disclosed subject matter in general terms, reference will now be made to the accompanying Drawings, which are not necessarily drawn to scale, and wherein:

FIG. 1 illustrates a top view of a foundation guide in accordance with an embodiment of the invention;

FIG. 2 illustrates a partial rear perspective view of the foundation guide in relation to a bone of an oral cavity in accordance with an embodiment of the invention;

FIG. 3 illustrates a partial top view of the foundation guide in relation to a bone of an oral cavity in accordance with an embodiment of the invention;

FIG. 4 illustrates another top view of the foundation guide seated on gum tissue in accordance with an embodiment of the invention;

FIG. 5 illustrates a partial top view of the circled section from FIG. 4;

FIG. 6 illustrates a portion of the foundation guide showing a close up view of tissue thickness indicators in accordance with an embodiment of the invention;

FIG. 7 illustrates a front view of the foundation guide and a stackable component prior to stacking the stackable component with the foundation guide in accordance with an embodiment of the invention;

FIG. 8 illustrates a partial rear view of the embodiment shown in FIG. 7;

FIG. 9 illustrates a front view of the foundation guide and the stackable component in a stacked configuration in accordance with an embodiment of the invention;

FIG. 10 illustrates a front perspective view of the embodiment shown in FIG. 9;

FIG. 11 illustrates a partial rear view of the embodiment shown in FIG. 9;

FIG. 12 illustrates example images of model matching of a patient's mouth;

FIG. 13 illustrates an example model image of diagnostic teeth in relation to bone;

FIG. 14 illustrates an example model image of the foundation guide prior to latching with a prosthesis FIG. 15 illustrates an example model image of the foundation guide latched with a prosthesis;

FIGS. 16-17 illustrate example model images of the foundation guide in relation to the mental foramen and nerve;

FIG. 18 and FIG. 19 illustrates a top axial view and front facial view, respectively, showing example dimensions of the foundation guide;

FIG. 20 illustrates an example of a bone model with a bone reduction plane;

FIG. 21 illustrates an example of a bone reduced model;

FIG. 22 illustrates another example of a bone reduced model altered to show placement and depths of planned implants and/or fixations;

FIG. 23 illustrates an example of glue holes and peg holes formed in a bone reduced model;

FIG. 24 illustrates an example of peg holes formed in a bone reduced model;

FIG. 25 illustrates an example of a tooth alignment guide;

FIG. 26 illustrates an example of a ridge alignment guide;

FIGS. 27 and 28 illustrate an example denture alignment guide;

FIG. 29 illustrates an example of a transfer mount; and

Figure 30:
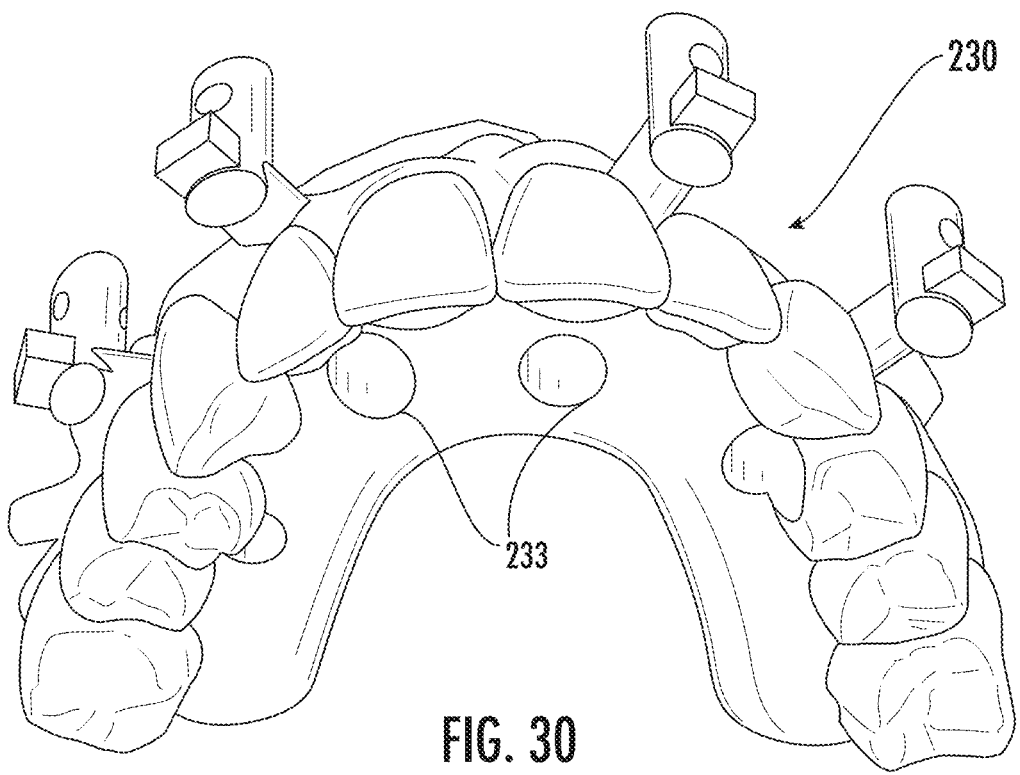

FIG. 30 illustrates an example of a latched PMMA.

DETAILED DESCRIPTION

The subject matter of the invention will now be described more fully hereinafter with reference to the accompanying Drawings, in which some, but not all embodiments of the subject matter are shown. Like numbers refer to like elements throughout. The subject matter of the invention may be embodied in many different forms and should not be construed as limited to the embodiments set forth herein; rather, these embodiments are provided so that this disclosure will satisfy applicable legal requirements. Indeed, many modifications and other embodiments of the invention set forth herein will come to mind to one skilled in the art to which the invention pertains having the benefit of the teachings presented in the foregoing descriptions and the associated Drawings. Therefore, it is to be understood that the invention is not to be limited to the specific embodiments disclosed and that modifications and other embodiments are intended to be included within the scope of the appended claims.

In some embodiments, the invention provides a unilateral tissue borne stackable foundation guide with tissue thickness indicators. In particular, the disclosed subject matter provides for a unilateral buccal mucosal borne stackable foundation stackable guide that includes tissue thickness indicators (hereinafter referred to as the "foundation guide"). The foundation guide is a surgical foundation that registers and seats to the buccal mucosa in the oral cavity of a patient, and may be anchored in place by anchoring to the maxillary or mandibular bone via fixation pins or screws. The foundation guide includes tissue thickness seating indicators, and may further include latches for supporting and securing surgical and prosthetic components and aligners. The tissue thickness indicators function to show the correct mucosal seating position when fixating the foundation guide to avoid over-tightening and compression of gum tissue. The foundation guide of the present disclosure provides a device for indicating tissue thickness of a patient and for supporting stackable components (surgical components, aligners, provisional and/or final dental prosthetics) during surgical procedures. The foundation guide of the present disclosure may operate as a foundation for, or a bone reduction guide, or act as bone reduction or scalloping guide, if bone contouring is required.

Using the presently disclosed foundation guide, surgery can be performed on dentate or edentulous patients, and with or without tissue reflection in both types of patients. The foundation guide is unilateral and thereby limits the amount of tissue reflection necessary to perform intra-oral surgery. Further, the foundation guide may be flat planed or scalloped for bone contouring and reduction. The presently disclosed foundation guide significantly reduces the invasive nature of intra-oral and dental implant surgical procedures.

Referring now to FIG. 1, is a top view of the presently disclosed foundation guide 100. FIG. 2 and FIG. 3 is a partial rear perspective and a partial top view, respectively, of the foundation guide in relation to a patient's bone in their oral cavity, and drawn without showing gum tissue. In one example, foundation guide 100 may include a main body 105, which may be curved in the general shape of a patient's gum line. Main body 105 may include connection sleeves 110 spaced about its outer surface 120, and may further include fixation ports 115 spaced about the curved body 105. Fixation ports 115 may form a passage through the main body 105 extending from the outer surface 120 through an inner surface 125 of the main body 105. In one example, the connection sleeves 110 and fixation ports 115 are spaced along the curved main body 105 in an alternating pattern. In one embodiment, curved body 105 includes four (4) connection sleeves 110 and three (3) fixation ports 115 evenly spaced apart in an alternating manner. Curved body 105 may include more or less than four (4) connection sleeves 110 and/or more or less than three (3) fixation ports 115. The connection sleeves 110 and fixation ports 115 are not limited to being evenly spaced apart in an alternating manner, and may be spaced at irregular intervals and/or may or may not be configured in an alternating arrangement with each other.

Foundation guide 100 may further include tissue thickness indicators 130. Tissue thickness indictors 130, in one example, these protrusions protrude outward in a generally perpendicular direction from the inner surface 125 of main body 105. Tissue thickness indictors 130 are preferably shaped to facilitate insertion into a patient's gum tissue. In one example, tissue thickness indicators 130 may be generally conical in shape, tapering to a point at their distal end. In one embodiment, tissue thickness indicators 130 may be localized in groups proximal to one or more of the fixation ports 115. As a non-limiting example, tissue thickness indicators 130 may be disposed generally about a periphery of one or more of the fixation ports 115. In one example, three (3) tissue thickness indicators 130 may be arranged around, and in proximity to, one or more of the fixation ports 115. It should be understood that there may be more or less than three (3) tissue thickness indicators 130, and further the tissue thickness indicators 130 may be disposed at other portions and/or in various configurations on the inner surface 125 of main body 105. Tissue thickness indictors 130 may vary in length depending on a specific patient. The length of the tissue thickness indicator 130 for a particular patient may be determined by the depth of the patient's gum tissue 135. In one example, the length of the tissue thickness indicator 130 for a particular patient is determined by measuring the space between the outer surface of the patient's gum tissue and their bone level below the gum tissue. The patient's gum tissue depth may be determined using any number of suitable techniques, for example, digital imaging and communications in medicine (DICOM) and stereo lithography (STL), and/or polyvinyl siloxane (PVS) intra-oral modeling, which may be done during a digital design phase of the foundation guide 100. The tissue thickness indicator 130 is preferably fabricated to be of a length that is shorter than the depth of the particular patient's gum tissue thickness, such that I does not engage the patient's underlying bone. In one non-limiting example, the tissue thickness indicator 130 may be of a length, such that it is in the range of about 0.3 mm shorter than the depth of the particular patient's gum tissue thickness. Tissue thickness indicators 130 are preferably not used as bone stops and are preferably purposefully fabricated to be shorter than the thickness of the patient's gum tissue. Rather, the tissue thickness indicators 130 are preferably of a length, such that when the foundation guide is fully and properly seated on a patient's gum tissue, the distal most ends of the tissue thickness indicators 130 fall short of contacting/engaging the patient's underlying bone. Thereby, providing the surgeon with a guide to help prevent the surgeon from over-tightening the guide, and compressing the gum tissue, when seating the foundation guide 100. That is, as the surgeon seats the foundation guide 100, he/she will know when to stop tightening based on the tissue thickness indicators, once the tissue thickness indicators reach their full depth into the gum tissue the surgeon knows to stop tightening.

The foundation guide 100 may be made of polymers, fiber reinforced material, Teflon reinforced nylon, carbon reinforced nylon polymer, nylon, fiberglass, HSHT fiberglass, carbon fiber, onyx, Kevlar, cobalt chrome, polymers, alloys, zirconias, printed resin material, nylon carbon fiber reinforced, and/or any other suitable material; and may be formed by printing, milling, casting, and/or any other suitable method/technique. The printing, milling, and/or casting of the foundation guide may be accomplished using various techniques/methods, e.g., axis milling systems, selective laser milling, digital laser milling, printed with resin based printer, centrifugal casted, digital precision metals (DPM), direct metal laser sintering (DMLS), and/or any other suitable methods and/or techniques. Further, the foundation guide 100 may be digitally designed with various suitable software packages and analog processed off, for example, SLT digital design files.

Referring now to FIGS. 4-6. FIG. 4, is a top view of the foundation guide 100 seat on a patient's gum tissue 135. FIG. 5 is a partial top view of the foundation guide 100 seat on a patient's gum tissue 135, and FIG. 6 is a view of a portion of the foundation guide 100 showing a close up view of tissue thickness indicators 130 formed thereon. In one embodiment, foundation guide 100 may be seated on the patients gum tissue and anchored in place by anchoring to the maxillary or mandibular bone 140 via fixation pins or screws 145.

Referring now to FIGS. 7-11. FIG. 7 and FIG. 8, is a front view and a partial rear view, respectively, of the foundation guide 100 and a stackable component 200 prior to stacking the stackable component 200 with the foundation guide 100. FIG. 9, FIG. 10, and FIG. 11 is a front view, top view, and a partial rear view, respectively, of the foundation guide 100 and a stackable component 200 in a stacked configuration. Foundation guide 100 and a stackable component 200 may be stacked together via one or more connection posts 205. Connection posts 205 are preferably sized and shaped, such that they may be received by connection sleeves 110 when the foundation guide 100 and a stackable component 200 are in a stacked configuration. In one example, one or more of connection sleeves 115 of the foundation guide 100 may include a first coupling pin hole 150 and one or more of the connection posts 205 of stackable component 200 may include a second coupling pin hole 250. The first coupling pin hole 150 and second coupling pin hole 250 may be configured, such that when the foundation guide 100 and the stackable component 200 are in the stacked configuration, with the connection posts 205 inserted in corresponding connection sleeves 115, the first coupling hole 150 and second coupling hole 250 are aligned with one another. The foundation guide 100 and the stackable component 200 may be secured in the stacked configuration by one or more coupling pins (not shown) inserted in corresponding first coupling pin holes 150 and second coupling pin holes 250. Foundation guide 100 and stackable component 200 may be stacked and secured together using any other suitable technique or mechanism, and is not limited to the connection sleeve 110 and connection post 205 configuration described above. Further, in an alternate embodiment, the connection sleeve 110 and connection post 205 configuration may be reversed, that is the connection post 205 may be present on foundation guide 100 in place of the connection sleeve 110, and connection sleeve 110 may be present on the stackable component 200 in place of the connection post 205.

In one example, foundation guide 100 may be made by first modeling a patient's mouth and importing the DICOM data and STL or PVS into the design software (See for example FIG. 12, which shows example model images of model matching of a patient's mouth). Once imported into the design software a diagnostic wax-up is performed and the case is surgically planned and reviewed with surgeon and or restorative clinician. After planning and review, the foundation guide 100, and other guides, e.g., stackable component 200, as may be needed may be designed digitally and analog processed. The stackable component 200 may be made of polymers, fiber reinforced material, Teflon reinforced nylon, carbon reinforced nylon polymer, nylon, fiberglass, HSHT fiberglass, carbon fiber, onyx, Kevlar, cobalt chrome, polymers, alloys, zirconias, printed resin material, nylon carbon fiber reinforced, and/or any other suitable material; and may be formed by printing, milling, casting, and/or any other suitable method/technique. The printing, milling, and/or casting of the stackable component 200 may be accomplished using various techniques/methods, e.g., axis milling systems, selective laser milling, digital laser milling, printed with resin based printer, centrifugal casted, digital precision metals (DPM), direct metal laser sintering (DMLS), and/or any other suitable methods and/or techniques. Further, the stackable component 200 may be digitally designed with various suitable software packages and analog processed off, for example, SLT digital design files.

In the case of an implant surgery, a stackable component 200, such as a surgical guide, are sleeved with appropriate implant sleeve guides 210 to allow for fully guided or pilot drilled surgery procedure. Once the foundation guide 100 and appropriate stackable component 200 is made, one or more coupling pin holes may be formed (drilled, printed, milled, or other suitable technique) through one or more corresponding connection sleeves 110 and connection posts 205, forming first coupling pin holes 150 and second coupling pin holes 250.

In a surgical procedure, in one example, a surgeon or clinician may position the foundation guide 100 on the gum tissue of a patient, and may secure with a tooth, tissue or bone borne aligner. A coupling pin may then be used to secure the foundation guide 100 with a stackable component 200 after seating the connection posts 250 of the stackable component 200 into corresponding connection sleeves 150 of the foundation guide 100. The surgeon or clinician may fixate the foundation guide 100 to the patients gum tissue 135, tightening until the tissue thickness indicators 130 show fully seated position. The fully seated position is shown when gum tissue 135 touches the inner surface 125 of the foundation guide 100 and the tissue thickness indicator 130 is fully submerged into the patient's gum tissue 135. After the foundation guide 100 is fully and properly seated, any surgical and/or prosthetic components, as may be needed, such as a surgical drill guide (See stackable component 200 in FIGS. 9-11), may be positioned and related to the foundation guide 100.

There are a number of distinctions and advantages of the presently disclosed foundation guide 100 over other devices currently in use. The foundation guide 100 is not seated directly on the patient's bone 140 but rather is positioned using the tissue thickness indicators 130 and held in position on the patient's gum tissue 135 with fixations pins or screws 145 anchored to the bone 140. Tissue thickness indicators 135 on the foundation guide 100 function to show the surgeon or clinician the correct buccal-lingual positioning depth. The height of the tissue thickness indicator 130 for a particular patient may be determined by measuring the space between the bone 140 level, which may be calculated using the intra-oral model in the digital design phase. The tissue thickness indicator 130 may be fabricated to be of a depth shorter than the patient's tissue thickness (e.g., in the range of about 0.3 mm). The tissue thickness indicators 130 are not bone stops and are purposefully fabricated to be shorter than the tissue 135 is thick. The foundation guide 100 is therefore a true tissue borne guide and not bone borne. By being a unilateral tissue borne guide with tissue thickness indicators 130 it protects the patient's buccal tissue 135 from necrosis during surgery resulting from compressing the tissue 135, which is often cause by overtightening guide screws. Further, with the present foundation guide 100, surgery can be performed with or without reflection of intra oral tissue, and when necessary to access the bone and surgical site it allows for use of a less invasive butterfly reflection technique, whereas other typical systems, e.g., bone borne or floating, depend on a more invasive buccal or buccal and lingual reflection of tissue. Using the foundation guide 100, tissue reflection, when required, may be done after seating of the foundation guide 100, whereas others base guide systems are seated after reflection of the tissue. The foundation guide 100 may be printed or milled from a true diagnostic work-up and processed in analog and digital workflow on an articular based set-up, e.g., upper and lower portions (foundation guide and stackable component 200) are joined together, whereas other systems are not processed on an analog mounted articulator. Referring to FIGS. 13-15, the foundation guide 100 system may latch the prosthesis in analog (not digital like other systems) making it possible to cross-mount and verify pre-operative and post-occlusion, and may double as a bite verification jig. Referring to FIGS. 16 and 17, the foundation guide 100 may further protect the mental foramen 155 and mental nerve (not shown) in the mandible during reflection and surgical procedures, for example, by a portion of the foundation covering the mental foramen 155 and mental nerve.

Referring now to FIG. 18 and FIG. 19, is a top axial view and front facial view, respectively, showing example dimensions of an example foundation guide 100. In one example, referring to FIG. 18, the thickness of foundation guide 100 along arrow 160 may be about 12 mm and the thickness of connection sleeve 110 along line 165 may be about 9 mm. Now referring to FIG. 19, the length of foundation guide 100 along arrow 170 may be about 63 mm; the width of fixation port 115 along arrow 175 may be about 6.5 mm; and the height of connection sleeve 110 along line 180 may be about 10 mm. The preceding are non-limiting examples only, and other dimensions greater or less than those in the examples, as may be required by a specific patient's oral measurements/model, are contemplated by the presently disclosed invention.

In one example, a diagnostic design of a foundation guide 100 may include initially preparing a diagnostic wax-up, which will become a temporary prosthetic. A physical impression of a patient's current oral anatomy, or a digital scan of the same, may be provided, e.g., by the requestor/client. The physical impression may be poured and scanned, and a digital model may be printed and scanned or imported resulting in a digital impression model. The diagnostic design may further include aligning the model of the patient's current oral anatomy to provided patient smile photos. Working within the parameters of the patient's existing dentition and bone structure, a prosthetic may be digitally planned to restore the patient's dental function and aesthetics. The restorative doctor and/or surgeon preferably consults with lab designers on prescribed changes, patient expectations, and possible restorative options. Any changes to vertical dimension of occlusion (VDO) or midline, existing dentition, and/or need for restorative space are all considered during diagnostic wax-up design. The aesthetic qualities of the planned restoration are considered and mocked-up by superimposing the diagnostic wax-up onto the patient's smile photos and may be sent back to the requestor/client for approval.

While opening the VDO may be necessary, failing to achieve a modest range may cause discomfort for the patient. Chosen restoration type and available restorative space may impact options for adjustment. A dual-arch prosthetic may correct the upper and lower, idealizing the patients bite. A single arch however, should preferably still be matched for occlusion against the patient's antagonist arch.

With regard to surgical planning, once the diagnostic wax-up is completed it may be imported by, for example, a guided surgery specialist to begin surgical planning. Surgical planning is based on laying a foundation for the prosthetic, which is derived from the diagnostic wax-up. In an embodiment, the foundation guide 100 design process is prosthetically driven, and the planned surgery is reverse engineered from the final prosthetic. Initially, the objective of the surgery is considered. For example, the final surgical plan may be for a removable, fixed hybrid, or partial restoration, which makes considerable differences in case planning. The patient's restorative space may determine the available room for the prosthetic, which may be increased by bone reduction if needed. For example, a removeable implant-supported denture may require significantly more restorative space as compared to a fixed hybrid. In addition, cleanse-ability of the final prosthetic is also considered as a quality of life concern for the patient. Working within the parameters of the patient's existing dentition and bone structure, the prosthetic is digitally planned to restore the patient's dental function and aesthetics. At this stage, a technician preferably plans out the final bite created by the prosthetic. The final bite, created when the prosthetic is loaded into the patient's mouth, is expected to match the patient's prescribed bite. In one example, implant placement may begin with the patient's cone-beam computed tomography (CBCT) scan, sent as a DICOM file, which is imported into a suitable planning software. The digital impression model, along with the digital model of the diagnostic wax-up, are imported and aligned to the CBCT scan. Planning considerations may include mapping out vital structures in the patient's mouth such as nerves, blood vessels, and areas of insufficient bone density. An implant site is preferably planned in areas of sufficient bone density, providing the best possible chance of achieving primary stability. Diameter and length of each implant are determined by the doctor's prescription and/or indications provided by the implant manufacturer. Implant size and type will determine the implant analogs, sleeving, and drill protocol used in the creation of the foundation guide 100, stackable components 200, and/or models.

With regard to planning fixation, fixation points may be chosen to anchor the foundation guide (foundation guide 100) or guides to the patient's existing bone structure. As in implant placement, important and vital structures need to be avoided. In addition, bone density should be sufficient to stabilize the foundation guide 100 across the patient's arch throughout the surgical procedure. Fixation points may be fixation pins or screws 145, such as pins, which may engage the patient's bone bi-cortically, or uni-cortical screws. Should fixations be planned over the roots of preexisting teeth, the tooth would preferably be extracted prior to guide seating, which would be communicated to the surgeon through documentation prior to surgery.

The foundation guide 100 may be well suited for cases in which there is enough bone for bi-cortical or uni-cortical fixation, sufficient vestibule size, sufficient mouth opening, and scans and/or models of sufficient detail and accuracy. The foundation guide 100 system's lack of required tissue reflection for guide seating may be well suited for cases with no or minimal bone reduction, as the total reflected area will be comparatively small. The foundation guide 100 system preserves tissue that may be needed for 'Scalloped' or 'Crown and Bridge' style cases, in which the prosthetic teeth sit directly on healed tissue.

With reference to FIGS. 20-24, in one example, a bone model 185 created from the CBCT scan may be constructed, imported, and aligned with the scan data. The bone model 185 may then be reduced to a bone reduction level by using a bone reduction plane 190 as a reference, creating a bone reduced model 193. This bone reduced model 193 may then be used in the creation of most guides (e.g., foundation guide 100) and components (e.g., stackable components 200). The bone reduced model 193 may then be altered to reflect the exact placement and depths of planned implants and/or fixations. Glue holes 195 may be placed to allow implant analogs to be permanently positioned into the model. Peg holes 197, may be placed to allow for seating of a transfer mount 220 or mounts. This new model (analog model) may then be 3-D printed and used by technicians to test the guides (e.g., foundation guide 100) and components (e.g., stackable component 200).

The initial foundation guide 100 preferably may sit typically in the range of about 2 mm off the bone model in order to be properly fixated during surgery. In order to create guides (e.g., stackable component 200) for the foundation guide 100 system, an additional bone model 185 may need to be created. A copy of the bone model 185 may be preferably created and offset by the same distance as planned for the foundation guide 100. The model surface may then be extended and maintains topographical consistency. This model, referred to as the offset model, may serve as a representation of the patient's tissue.

The foundation guide 100 may be created by mapping fixation bodies (e.g., fixation ports 115) across the offset model. Fixation ports 115 may include a cylindrical opening, e.g., in the range of about 8 mm in diameter, surrounded with geometry mapped to the patient's tissue as it is represented in the offset model. This geometry covers the facial arc of the surgical site. The fixation ports 115 may serve as a fit for anchorage pieces such as fixation pins or screws 145. The incisal surface of the foundation guide 100 preferably levels with the bone reduction plane 190, and may serve as a reference for bone reduction.

For the purposes of creating and utilizing stackable guides (e.g., stackable component 200), jack (e.g., connection posts 205) and plug (e.g., connection sleeves 110) style latches/connectors, for example three (3) or more, may be formed around the facial arc of the bone model 185. In some examples, the connection posts 205 and connection sleeves 110 latches/connectors may be respectively referred to as male and female latches/connectors. The connection sleeve 110 surfaces may sit on the bone reduction plane 190. This will allow sufficient vestibule room for the foundation guide 100 to seat comfortably. The connection sleeve 110 surfaces at the bone reduction plane 190 may now also serve as a guide for bone reduction.

Tissue thickness indicators 130, in one embodiment, may be spike-like protrusions attached about each fixation port 115. Tissue thickness indicators 130 are preferably configured to pierce through the patient's tissue, stopping prior to engaging the patient's underlying bone structure. The foundation guide 100 may be affixed to the patient with little to no tissue reflection, greatly reducing the invasive nature of traditional surgical guides. The tissue thickness indicators 130 may be positioned on the lingual side (inner surface) of the foundation guide 100 and carefully positioned so that they do not interfere with the fixation's trajectory. The tissue thickness indicators 130 preferably act in conjunction with an aligner (such as an alignment guide) to stabilize the foundation guide 100 during fixation. Fixation screws (e.g., fixation pins or screws 145) may be used to tighten the foundation guide 100 while the tissue thickness indicators 130 help prevent crushing of the patient's tissue.

Seating guides may be created from a digital impression, which may include teeth, a tissue ridge, and/or a denture, or a converted CBCT model depicting the patient's relevant bone. This model may be aligned to the patient's existing dental anatomy as pictured in the CBCT. These models may then used to create seating guides, which may include, for example, tooth alignment guide 205, ridge alignment guide 210, denture alignment guide 215 (as shown for example in FIGS. 25, 26, 27, 28). The initial construction of such seating guides may differ and non-limiting examples are described below.

With reference to FIG. 25, illustrates an example tooth alignment guide 205. In cases where a patient has existing teeth that are suitable for building guides, the digital impression model may be used to create a tooth alignment guide 205. The initial tooth alignment guide 205 may be created by enveloping the digital impression model with a polygonal mesh so that its internal structure matches the topography of the dentition with a defined offset, e.g., about 0.15 mm, in one example, its external structure may be about 3-4 mm in thickness. In some cases, it may be necessary to plan for tooth extraction before guide fixation. Instances where this is a factor may include situations where fixations may be placed through a tooth root, or where teeth are so badly damaged that they are unusable for the tooth alignment guide 205. In these cases, either the .stl based on the digitized scan of the patient's digital impression model should be altered to reflect these extractions, or special care should be taken to avoid these obstructions during the envelopment phase. For visibility, cylindrical holes commonly referred to as "windows" (e.g., windows 207), may be cut into the guide, allowing the surgeon to see the patient's existing teeth and/or tissue, and allows confirmation of accurate seating. The tooth alignment guide 205 may then be cut on the lingual side in order to reduce the total guide size if needed. The distal edges may also be removed to reduce the tooth alignment guide 205 size further if needed.

With reference to FIG. 26, illustrates an example ridge alignment guide 210. In cases where the patient has no existing teeth for suitable guide building, a ridge alignment guide 210 may be created by enveloping the .stl model of the patient's CBCT scan with a polygonal mesh so that its internal structure matches to the patient's bone structure, with an offset typically of about 0.15 mm. Its external structure, in one example, may be about 3-4 mm thick. Cylindrical holes 213 may then be cut, allowing the surgeon to see the bone structure and confirm accurate seating. The ridge alignment guide 210 may also be trimmed appropriately as/if needed.

With reference to FIGS. 27 and 28, illustrate an example denture alignment guide 215. In cases where the patient has an existing and well-fitting denture, a denture alignment guide 215 may be used. A digitized scan of the patient's existing denture may be converted to a .stl mesh. Cylindrical holes 217 may then be cut into the denture alignment guide 215, allowing the surgeon to see the palatal tissue and confirm seating. Some trimming may be necessary; however, the denture's structure should be kept intact.

With reference to FIG. 29, illustrates an example transfer mount 220. Transfer mount 220 may have cylindrical pegs 223 corresponding to each punched port on the analog model. In one non-limiting example, each cylindrical peg 223 may be $\frac{1}{10}$ of 1 mm smaller in diameter to its related port so that it fits securely after the transfer mount 220 has been affixed to the analog model. For testing the mounted analog and transfer mount 220 are fixed to a bite verification jig (not shown), the device fits and measures the mounted analog against a printed model of the patient's opposing arch. This measurement will be used to test the accuracy and effectiveness of the temporary prosthetic. If the prosthetic is accurate, the measurement will be the same.

The foundation guide 100 and tooth alignment guide 205 may be tested in a manner similar to their surgical use. The transfer mount 220 may be inserted into the analog model and foundation guide 100 may be latched and pinned to the tooth alignment guide 205. This assembly is used to deliver the foundation guide 100 onto the transfer mount 220 and analog model. When placed onto the analog model the tissue thickness indicators 130 will not contact the analog model. This may necessitate some additional stabilization when testing the foundation guide 100, as there is no tissue on the model with which to seat. Due to fixation ports 115 already being created during the design phase, the foundation guide 100 can be fixated to the model with fixation pins or screws 145.

Each of the stackable components 200 may be inserted into the foundation guide 100 for testing and inspected for fit and functionality. Each combination of connection post 205 on the stackable components 200 is latched to the connection sleeves 110 on the foundation guide 100 using, for example, removable coupling pins (e.g., 2 mm coupling pins). This allows each stackable components 200 to be firmly attached to the foundation guide 100 without fear of any unwanted movement during the surgery. In some cases, if the coupling pin fit is too tight, it may be necessary using a hand piece or rotary tool to expand the diameter of the coupling pin holes 150/250 on both the connection sleeves 110 and/or the connection posts 205. Basic functionality of each of the guides may also be tested.

For testing a stackable drill guide component 225, the stackable drill guide component 225 may be sleeved and test-fit by fixating the foundation guide 100 to the analog model and latching the stackable drill guide component 225 into the foundation guide 100. Once accurate and secure seating has been confirmed the stackable drill guide component 225 may be removed from the foundation guide 100, it is now possible to "time out" the case.

With reference to FIG. 30, as the foundation guide 100 system is prosthetically driven, the case can be "timed" with the use of a latched PMMA 230, as it is a stand-in for the temporary prosthetic. The foundation guide 100 may be fixated onto the analog model. Implant analogs may then be placed into the analog model, and any abutments and temporary cylinders may be attached. The latched PMMA 230 may be latched into the foundation guide 100. As the planned emergence is represented in holes 233 through the latched PMMA 230, the technician may align the temporary cylinder with the emergence hole 233 by rotating the implant-abutment-temporary cylinder complex. Once each temporary cylinder matches its planned emergence, the implant analogs may be glued in position. The latched PMMA 230, temporary cylinders, and abutments may then be removed, leaving the implant analogs glued into the analog model at the correct planned rotation. The stackable drill guide component 225 may then be latched into the foundation guide 100, an implant driver may be inserted through a sleeve guide 210 into an implant. A marking may be made on the stackable drill guide component 225 at each implant site corresponding to a marking on the implant driver. During surgery, the implant will be driven in, torqued, and the driver rotated to match this marking. This will set the emergence as planned.

In one example, for testing guides (e.g., seating guide, bone reduction guide, abutment alignment guide), they each may be separately fixated to the foundation guide 100 and checked for fit and sturdiness. Timing marks may be etched and stained into one or more of the guides as desired (e.g., abutment alignment guide). Once each piece has been verified for accuracy it may be removed and prepped to be shipped for the surgery.

For finishing bite verification with the latched PMMA 230, the transfer mount 220 may be removed from the analog model and a latched PMMA 230 may then be latched into the foundation guide 100. The analog model, fitted with the foundation guide 100 and latched PMMA 230, may then be inserted into the bite verification jig where it will be tested against the printed model of the patient's opposing arch. The measurement output should preferably not change from the prescribed bite. Each guide piece may be inspected and corrected if necessary. Finally, the finished temporary prosthetic may be set into the bite on the verification jig in place of the latched PMMA 230. Individual connection posts 205 latches are preferably pinned into corresponding connection sleeves 105 of the foundation guide 100 and cemented to the temporary prosthetic. This will allow the prosthetic to be delivered by latching into the foundation guide 100 and cementing in temporary cylinders. During surgery, once the temporary cylinders are cemented, the prosthetic may be removed from the mouth, the latches cut off, and the temporary prosthetic loaded onto the implants. Once the bite has been verified for accuracy and the entire foundation guide 100 kit has passed quality control, all guides, models, and components may then be prepped and packed for shipping.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:
1. A foundation guide, comprising:
   a. a main body;
   b. first connectors spaced about the main body, wherein the first connectors are connected to the main body at an upper portion of the first connectors and a lower portion of the first connectors extend below a lower surface of the main body, and wherein each of the first connectors comprise a connection sleeve comprising a vertically extending cylindrical passageway therethrough;
   c. fixation ports spaced about the main body, the fixation ports forming a passage through the main body; and
   d. protrusions formed on an inner surface of the main body and extending in a generally perpendicular direction therefrom, wherein the protrusions are disposed proximate to and distributed at least partially about a periphery of each of the fixation ports.

2. The foundation guide of claim 1, wherein the protrusions comprise conical shaped bodies tapering to a point at a distal end, and are distributed at least partially about the periphery of each of the fixation ports in a generally triangular pattern.

3. The foundation guide of claim 1, wherein the protrusions comprise a length, such that when the foundation guide, configured to be seated on a patient's gum tissue, is fully seated on the patient's gum tissue distal ends of the protrusions do not engage underlying bone of the patient.

4. The foundation guide of claim 1, wherein the fixation ports are configured to receive a device therethrough for fixating and anchoring the foundation guide to a maxillary or mandibular bone of a patient.

5. The foundation guide of claim 4, wherein the device comprises at least one of a fixation pin and screw.

6. The foundation guide of claim 1, wherein the first connectors each comprise a first coupling hole, wherein the first coupling hole forms a passageway through the first connector that is substantially perpendicular to a length of the first connector.

7. The foundation guide of claim 1, wherein the main body comprises a generally curved shape in a general shape configured to be located on a gum line of a patient.

8. The foundation guide of claim 1, further comprising a stackable component, the stackable component comprising:
a. a component body; and
b. second connectors spaced about an outer edge of the component body, wherein the second connectors are configured to engage with the first connectors.

9. The foundation guide of claim 8, wherein the second connectors each comprise a second coupling hole, wherein the second coupling hole forms a passageway through the second connectors that is substantially perpendicular to a length of the second connector.

10. The foundation guide of claim 9, wherein the first connectors and second connectors are configured such that when engaged the second connectors seat into voids formed in corresponding ones of the first connectors, and wherein when the second connectors are seated into the first connectors, the second coupling holes are aligned with first coupling holes formed in the first connectors.

11. The foundation guide of claim 10, wherein the stackable component is secured to the foundation guide via one or more coupling mechanisms inserted through the aligned first and second coupling holes.

12. The foundation guide of claim 8, wherein the stackable guide is configured to facilitate a dental procedure.

13. The foundation guide of claim 12, wherein the stackable guide further comprises one of a surgical component or a prosthetic component formed thereon.

14. A foundation guide, comprising:
a. a main body;
b. first connectors spaced about the main body, wherein the first connectors are connected to the main body at an upper portion of the first connectors and a lower portion of the first connectors extend below a lower surface of the main body, and wherein each of the first connectors comprise a connection sleeve comprising a vertically extending cylindrical passageway therethrough, and wherein the first connectors are generally uniform in shape and size;
c. fixation ports, the fixation ports forming a passage extending from an outer surface of the main body through an inner surface of the main body, the fixation ports configured for receiving a fixation mechanism for fixating the foundation guide to a patient's bone; and
d. protrusions formed on the inner surface of the main body and extending in a generally perpendicular direction therefrom, wherein the protrusions are disposed proximate to and distributed about a periphery of each of the fixation ports.

* * * * *